(12) United States Patent
Liu et al.

(10) Patent No.: US 12,270,124 B2
(45) Date of Patent: Apr. 8, 2025

(54) METHOD FOR SCREENING PROTEASE VARIANT AND OBTAINED PROTEASE VARIANT

(71) Applicant: SHANGRAO CONCORD PHARMACEUTICAL CO., LTD, Shangrao (CN)

(72) Inventors: Rikui Liu, Shangrao (CN); Xiaolong Zou, Shangrao (CN); Jianghua Wan, Shangrao (CN)

(73) Assignee: SHANGRAO CONCORD PHARMACEUTICAL CO., LTD, Shangrao (CN)

( * ) Notice: Subject to any disclaimer, the term of this patent is extended or adjusted under 35 U.S.C. 154(b) by 941 days.

(21) Appl. No.: 17/277,204

(22) PCT Filed: Jan. 11, 2019

(86) PCT No.: PCT/CN2019/071417
§ 371 (c)(1),
(2) Date: Mar. 17, 2021

(87) PCT Pub. No.: WO2020/073553
PCT Pub. Date: Apr. 16, 2020

(65) Prior Publication Data
US 2022/0025355 A1   Jan. 27, 2022

(30) Foreign Application Priority Data
Oct. 10, 2018 (CN) .......................... 201811177105.9
Dec. 17, 2018 (CN) .......................... 201811540344.6

(51) Int. Cl.
*C40B 30/08* (2006.01)
*C12N 15/10* (2006.01)

(52) U.S. Cl.
CPC .......... *C40B 30/08* (2013.01); *C12N 15/1037* (2013.01)

(58) Field of Classification Search
None
See application file for complete search history.

(56) References Cited

U.S. PATENT DOCUMENTS

| 9,546,359 B2 | 1/2017 | Iverson et al. |
| 2010/0035300 A1 | 2/2010 | Wang et al. |
| 2011/0251073 A1 | 10/2011 | Cascao-Pereira et al. |

FOREIGN PATENT DOCUMENTS

| CA | 2791144 A1 | 4/2008 |
| CN | 102822196 A | 12/2012 |

(Continued)

OTHER PUBLICATIONS

Fang, J., "Construction and Characteristic Analysis of TEV Protease Mutant, Full-text Database of China's Outstanding"; Thesis, China Academic Journal Electronic Magazine Press, 2016 vol. 4, A006-186, published Mar. 16-Apr. 15, 2016. ISSN 1674-0246 CN 11-9144/G.

(Continued)

*Primary Examiner* — Christian C Boesen
(74) *Attorney, Agent, or Firm* — Fox Rothschild LLP

(57) ABSTRACT

The present invention relates to a method for screening a protease variant and the obtained protease variant, and the protease variant has a special performance. The method for screening the protease variant comprises the following steps: (1) constructing a protease random mutation library, optimizing a protease random mutation virus library, and optimizing a protease random mutation phage library; (2) for the protease random mutation library, optimizing the protease random mutation virus library, and optimizing the protease random mutation phage library and screening a protease variant having weak protease enzyme-cutting activity in a (Continued)

host or a similar condition and having protease enzyme-cutting activity in an in vitro denaturation condition; and (3) the step of optionally characterizing the protease variant, wherein the protease optimizes TEV protease or enterokinase. The protease variant in the present invention facilitates industrial production of protein.

10 Claims, 6 Drawing Sheets

Specification includes a Sequence Listing.

(56) References Cited

FOREIGN PATENT DOCUMENTS

| CN | 105669856 A | 6/2016 |
|---|---|---|
| EP | 1361284 A1 | 11/2003 |
| WO | 2006108826 A1 | 10/2006 |
| WO | 2011091370 A1 | 7/2011 |

OTHER PUBLICATIONS

Sun, C. et al., "Tobacco Etch Virus Protease Retains its Activity in Various Buffers And In The Presence of Diverse Additives"; Protein Expression and Purification (2012); Vo. 82; pp. 226-231.

Huai, Z. et al., "The Vecotor Construction, Expression and Preparation of Hepcidin In *Escherichia coli*"; Beijing University of Chemical Technology (2005); (Part 1, 43 pgs of) 127 pgs.

Huai, Z. et al., "The Vecotor Construction, Expression and Preparation of Hepcidin In *Escherichia coli*"; Beijing University of Chemical Technology (2005); (Part 2, 43 pgs of) 127 pgs.

Huai, Z. et al., "The Vecotor Construction, Expression and Preparation of Hepcidin In *Escherichia coli*"; Beijing University of Chemical Technology (2005); (Part 3, 41 pgs of) 127 pgs.

Li, G. et al., "A Simple Method for Recombinant Protein Purification Using Self-assembling Peptide Tagged Tobacco Etch Virus Protease"; Protein Expression and Purification (2016); vol. 128; pp. 86-92.

Achmuller, C. et al., "Npro Fusion Technology to Produce Proteins with Authentic N Termini in *E. coli*"; Nature Methods (2007); vol. 4:12 pp. 1037-1043.

Guerrero, J. et al., "Emerging Technologies for Protease Engineering: New Tools to Clear Out Disease"; Biotechnology and Bioengineering (2017); vol. 114:1; pp. 33-38.

Yu, X. et al., "Assessment of the Fusion Tags on Increasing Soluble Production of the Active TEV Protease Variant and Other Target Proteins in *E. coli*"; Appl Biochem Biotechnol (2017); vol. 182; pp. 769-781.

Yu, X. et al., "Tobacco etch virus protease mediating cleavage of the cellulose-binding module tagged colored proteins immobilized on the regenerated amorphus celloluse"; Bioprocess Biosyst Eng (2017); vol. 440; pp. 1101-1110.

Yi, L. et al., "Engineering of TEV protease variants by yeast ER sequestration screening (YESS) of combinatorial libraries"; PNAS (2013); vol. 110:18; pp. 7229-7234.

"Tobacco etch virus protease variant L56V/S135G/S219N, SEQ ID 17"; GENESEQ (2011).

Extended European Search Report issued on Apr. 21, 2022 for European Patent Application No. 19870712.7 (15 pages).

METHOD FOR SCREENING PROTEASE VARIANT AND OBTAINED PROTEASE VARIANT

CROSS-REFERENCE TO RELATED APPLICATIONS

This application is a U.S. National Phase of International Application No. PCT/CN2019/071417, filed Jan. 11, 2019, which claims the priority benefit of the Chinese invention patent application with the application No. 201811177105.9, titled "TEV protease variant, fusion protein, preparation method and use thereof" submitted on Oct. 10, 2018 and the Chinese invention patent application with the application No. 201811540344.6, titled "method for screening protease variant and obtained protease variant" submitted on Dec. 17, 2018, which are incorporated in their entireties by reference.

REFERENCE TO SEQUENCE LISTING SUBMITTED ELECTRONICALLY

This application contains a sequence listing, which is submitted electronically via EFS-Web as an ASCII formatted sequence listing with a file name "145954.01500_SeqList2" and a creation date of Feb. 2, 2024, and having a size of 22.8 kb. The sequence listing submitted via EFS-Web is part of the specification and is herein incorporated by reference in its entirety.

TECHNICAL FIELD

The present invention relates to the field of protein, in particular to a method for screening TEV protease variants and TEV protease variants.

BACKGROUND

A TEV protease is a 27 kDa active domain derived from tobacco etch virus (TEV) N1a protease, and its amino acid sequence is shown in SEQ ID NO: 1. The TEV protease has strong site specificity and can recognize the seven-amino acid sequence of EXXYXQ (G/S) (SEQ ID NO: 9 or SEQ ID NO: 11). The most common sequence is Glu-Asn-Leu-Tyr-Phe-Gln-Gly (or ENLYFQG) (SEQ ID NO: 29) with a restriction site between glutamine Gln (P1) and glycine Gly (P1') (i.e., between P1 and P1'). The sequence specificity of the TEV protease is far higher than that of proteases such as thrombin, factor Xa, and enterokinase.

The TEV protease can tolerate a wide range of pH (pH 4-8.5) and temperature (4-34° C.), and has varying degrees of tolerance to some common additives that increase protein solubility or stability (ethylene glycol, EGTA, detergents and reducing agents). There are studies which show that the TEV protease is not sensitive to ethylene glycol, EGTA and some detergents (Triton X-100, Tween-20, and NP-40). In presence of 1% CHAPS, the activity is decreased and in presence of a low concentrations of a denaturant (2 M urea, 1% SDS) and a reducing agent (0.7 M β-mercaptoethanol), most of the activity can still be maintained (C. Sun et al., 2012).

The wild-type TEV enzyme has certain defects in expression and solubility, so there are a large number of reports on mutants improved by genetic engineering technology. For example, self-cleavage will occur for a natural TEV protease. During the expression and purification process, the TEV protease will continue to undergo conformational changes due to collision with other TEV proteases, and self-cleave at specific sites, so that the intact protease is truncated and its activity is greatly reduced. The S219N mutant found by Lucast et al. has greatly improved stability, but its solubility is not high, and about 95% of the protein is present in the precipitate in form of inclusion bodies. Kapust et al. made point mutations in the gene sequence of the natural TEV protease using genetic engineering, and obtained S219V, a mutant with higher stability and slightly improved enzyme activity, the stability of which was about 100 times higher than that of S219N. Secondly, the expression yield of TEV protease is not high, and the solubility is also very low. Only about 5% of TEV protease is present in the supernatant of the cell disruption solution, with the yield of 12.5 mg/L. Van den Berg et al. found a mutant TEVSH, the yield of which can be increased to 54 mg/L, through DNA shuffling and error-prone PCR and the solubility of the mutant was much higher than that of S219N, with little change in enzyme activity. Cabrita, L. D. et al. analyzed TEV protease single-point mutants for stability using design by PoPMuSiC software, and screened out five mutants, the solubility and enzyme activity of which were improved compared with wild-type TEV protease, and a double mutant was obtained at the same time, with solubility and enzyme activity significantly improved compared to the single mutant. In view of the shortcomings of TEV protease itself, researchers have been looking for improved mutants. For example, TEV Ser135Gly mutant is more stable than WT and can tolerate higher temperatures (>40° C.). There are also some mutations (T17S, N68D, or N177V) that can significantly increase the solubility of TEV protease.

The current methods for screening the TEV protease mainly focus on improving the properties of the TEV protease, such as enzymatic activity, solubility and yield. The method for screening the TEV protease as in this application has not been reported yet.

SUMMARY OF THE INVENTION

The present invention is based, at least partially, on the findings of the inventors during the production of polypeptide drugs that: at present, a conventional TEV protease will cleave (self-cleavage) a large amount of fusion protein during the expression process, resulting in the pre-release of the polypeptide, which is easily hydrolyzed by an intracellular protease, which is not conducive to purification and is not suitable for industrial production; although a conventional TEV protease can maintain most of its activity in low concentrations of denaturants (2 M urea, 1% SDS) (C. Sun et al., 2012), many proteins cannot be completely dissolved under low concentration denaturation conditions such as 2M urea, which limits the use of TEV protease. In this regard, the inventors provided the following new screening methods to look for the TEV protease variants suitable for solving this problem.

The present invention provides a method for screening a protease variant comprising the following steps:
  (1) constructing a library of protease random mutations, preferably a virus library of protease random mutations, preferably a phage library of protease random mutations;
  (2) screening the library of protease random mutations, preferably the virus library of protease random mutations, preferably the phage library of protease random mutations for a protease variant that has a weak enzymatic cleavage activity of a protease in a host or under similar conditions and has an enzymatic cleavage activity of a protease under extracellular denaturation conditions; and (3) optionally the step of characterizing the protease variant, wherein the protease is preferably a TEV protease or an enterokinase.

In one embodiment, the method further comprises generation of the library of mutations using a random mutation kit.

In one embodiment, in step (1) random mutations are made with a suitable protease template, such as a TEV protease template, such as S219V TEV protease having the amino acid sequence as shown in SEQ ID NO: 10 as the template to construct the library.

In one embodiment, the protease variant has a lower enzymatic cleavage activity in a host or under similar conditions than the initial protease and retains the enzymatic cleavage activity of the initial protease under extracellular denaturation conditions.

In one embodiment, the TEV protease variant has a lower enzymatic cleavage activity in a host or under similar conditions than the S219V protease having the amino acid sequence as shown in SEQ ID NO: 10 and retains the enzymatic cleavage activity of the S219V protease having the amino acid sequence as shown in SEQ ID NO: 10 under extracellular denaturation conditions.

In one embodiment, the protease variant, preferably a TEV protease variant is displayed in the form of a fusion protein comprising a protease-protease cleavage sequence-Y1, such as TEVp-sTEV-Y1, preferably the protease variant, preferably a TEV protease variant being displayed on a phage, wherein TEVp is the TEV protease variant, sTEV is the cleavage sequence of the TEV protease, and Y1 is the protein of interest; preferably wherein the cleavage sequence of the TEV protease is EXXYXQG/S/H (SEQ ID NO: 30), wherein X is any amino acid residue, and preferably wherein the cleavage sequence of the TEV protease is selected from SEQ ID NOs: 7 and 8.

In one embodiment, the method comprises addition of a moiety A to the N-terminus of the protease variant, preferably the TEV protease variant, directly or indirectly via a linker in a host.

In one embodiment, the moiety A is one of the following: affinity tag, biotin, antibody, antigen, hapten, poly-streptavidin, ligand, receptor, nucleic acid, enzyme, substrate and aptamer.

In one embodiment, the method comprises incubating the phage library added with the moiety A with a solid support immobilized with a moiety B specific for the moiety A under extracellular conditions suitable for the protease for a period of time, and separating the support from the solution containing the target phage, optionally repeating the screening of the target phage one or more times.

In one embodiment, the moiety B is one of the following: biotin, antibody, antigen, hapten, polystreptavidin, ligand, receptor, nucleic acid, enzyme, substrate and aptamer, provided that the moiety B specifically binds moiety A.

In one embodiment, the protease, preferably the TEV protease is displayed at the terminus of the phage PIII protein in the form of Avi-protease-protease cleavage site-Y1-PIII, preferably Avi-TEVp-sTEV-Y1-PIII through a pHEN1-Avi-TEVp-sTEV-Y1 construct, wherein Avi tag is a short peptide tag composed of 15 amino acid residues (GLNDIFEAQKIEWHE, SEQ ID NO: 35); preferably, wherein the cleavage sequence of the TEV protease is EXXYXQG/S/H (SEQ ID NO: 30), wherein X is any amino acid residue, preferably the cleavage sequence of the TEV protease being selected from SEQ ID NOs: 7 and 8.

In one embodiment, the enzymatic cleavage activity is determined on a fusion protein comprising the protease and its cleavage sequence, such as protease-protease cleavage sequence-Y1, preferably comprising the TEV protease variant and its cleavage sequence, preferably TEVp-sTEV-Y1.

In one embodiment, the screening comprises biotinylation of the phage library of the protease random mutations, preferably the TEV protease random mutations in a host.

In one embodiment, the screening comprises treating the biotinylated phage library with streptavidin magnetic beads, incubating the phage captured by the magnetic beads in a moderate to high concentration of urea for a period of time, and separating the magnetic beads from the solution containing the target phage, optionally repeating the screening of the target phage one or more times.

In one embodiment, the library is verified by a colony PCR. In one embodiment, the primer used for the colony PCR is:

forward primer: 5'-CCACCATGGCCGGTCTGAATGA-TATTTTTGAAGC-3' (SEQ ID NO: 39)
reverse primer: 5'-TTGTTCTGCGGCCGCAAAT-TCCAGC-3' (SEQ ID NO: 40).

In one embodiment, the capacity of the library is up to $1 \times 10^9$ or more, preferably $2 \times 10^9$; preferably, the overall mutation frequency is a moderate to low degree of 1.5-7/kb.

In one embodiment, Y1 is human or porcine ACTH or GLP-1. In one embodiment, the host is *Escherichia coli*.

In one embodiment, the extracellular denaturation conditions are a moderate to high degree of denaturation conditions, preferably under the condition of 3 M-5 M urea, preferably 3.5 M-4.5 M urea, more preferably 4 M urea or 1 M-2 M guanidine hydrochloride, preferably 1.5 M guanidine hydrochloride.

The present invention provides a protease variant obtained by the method of the present invention. In one embodiment, the protease variant has a low enzymatic cleavage activity during expression in a host, preferably the TEV protease variant having a lower enzymatic cleavage activity than the S219V variant having the amino acid sequence as shown in SEQ ID NO: 10, the cleavage sequence of the TEV protease being selected from EXXYXQG/S/H (SEQ ID NO: 30), wherein X is any amino acid residue, preferably the cleavage sequence of the TEV protease being selected from SEQ ID NOs: 7 and 8; preferably the protease variant or the TEV protease variant retains the extracellular enzymatic cleavage activity of the initial protease such as the S219V protease under a moderate to high degree of denaturation conditions, preferably in an extracellular environment of 3 M-5 M urea, preferably 3.5 M-4.5 M urea, more preferably 4 M urea or 1 M-2 M guanidine hydrochloride, preferably 1.5 M guanidine hydrochloride; preferably, the enzymatic cleavage activity is determined on a fusion protein comprising the protease variant and its cleavage sequence, such as protease-protease cleavage sequence-Y1, preferably comprising the TEV protease variant and its cleavage sequence, preferably the cleavage sequence of the TEV protease being EXXYXQG/S/H (SEQ ID NO: 30), wherein X is any amino acid residue, preferably the cleavage sequence of the TEV protease being selected from SEQ ID NOs: 7 and 8.

In one embodiment, the TEV protease variant comprises one or more mutations selected from the group consisting of:
the mutation from leucine (L) to phenylalanine (F) or histidine (H) at the position corresponding to position 111 of the sequence shown in SEQ ID NO: 1;

the mutation from isoleucine (I) to lysine (K) at the position corresponding to position 138 of the sequence shown in SEQ ID NO: 1;

the mutation from histidine (H) to leucine (L) at the position corresponding to position 28 of the sequence shown in SEQ ID NO: 1;

the mutation from glutamic acid (Q) to histidine (H) at the position corresponding to position 196 of the sequence shown in SEQ ID NO: 1;

the mutation from serine(S) to glycine (G) at the position corresponding to position 135 of the sequence shown in SEQ ID NO: 1; and the mutation from methionine (M) to isoleucine (I) at the position corresponding to position 187 of the sequence shown in SEQ ID NO: 1;

preferably, wherein the TEV protease variant comprises a combination of mutations selected from:

the mutation from leucine (L) to phenylalanine (F) at the position corresponding to position 111 of the sequence shown in SEQ ID NO: 1 and the mutation from isoleucine (I) to lysine (K) at the position corresponding to position 138 of the sequence shown in SEQ ID NO: 1;

the mutation from histidine (H) to leucine (L) at the position corresponding to position 28 of the sequence shown in SEQ ID NO: 1, the mutation from leucine (L) to phenylalanine (F) at the position corresponding to position 111 of the sequence shown in SEQ ID NO: 1 and the mutation from glutamic acid (Q) to histidine (H) at the position corresponding to position 196 of the sequence shown in SEQ ID NO: 1; and the mutation from leucine (L) to histidine (H) at the position corresponding to position 111 of the sequence shown in SEQ ID NO: 1, the mutation from serine(S) to glycine (G) at the position corresponding to position 135 of the sequence shown in SEQ ID NO: 1 and the mutation from methionine (M) to isoleucine (I) at the position corresponding to position 187 of the sequence shown in SEQ ID NO: 1; preferably, the TEV protease variant comprises the mutation from serine(S) to valine (V) at the position corresponding to position 219 of the sequence shown in SEQ ID NO: 1; preferably, wherein the TEV protease further comprises one or more mutations other than the mutations described above, provided that the TEV protease variant has a low enzymatic cleavage activity during expression in a host, preferably having a lower enzymatic cleavage activity than the S219V variant having the amino acid sequence shown in SEQ ID NO: 10 and/or the TEV protease variant has a high enzymatic cleavage activity, preferably retaining an extracellular enzymatic cleavage activity of the S219V variant under a moderate to a high degree of denaturation conditions, preferably in an extracellular environment of 3 M-5 M urea, preferably 3.5 M-4.5 M urea, more preferably 4 M urea or 1 M-2 M guanidine hydrochloride, preferably 1.5 M guanidine hydrochloride.

In one embodiment, the homologue comprises an amino acid sequence having at least 90%, preferably at least 95%, more preferably at least 98%, and most preferably at least 99% sequence identity with SEQ ID NO: 4, 5 or 6; preferably, wherein the homologue comprises an amino acid sequence having at least 1, preferably at least 2, more preferably at least 3, and most preferably at least 4 substitutions, deletions or additions at (an) amino acid site(s) as compared with SEQ ID NO: 4, 5 or 6; preferably, wherein the homologue has a low enzymatic cleavage activity during expression in a host, preferably having a lower enzymatic cleavage activity than the S219V variant having the amino acid sequence shown in SEQ ID NO: 10 and/or the TEV protease variant retains extracellular enzymatic cleavage activity of S219V variant under a moderate to high degree of denaturation conditions, preferably in an extracellular environment of 3 M-5 M urea, preferably 3.5 M-4.5 M urea, more preferably 4 M urea or 1 M-2 M guanidine hydrochloride, preferably 1.5 M guanidine hydrochloride.

The present invention provides a fusion protein. The fusion protein comprises the protease variant according to the present invention; preferably the fusion protein comprises the structure of protease-protease cleavage sequence-Y1, preferably TEVp-sTEV-Y1, wherein Y1 is the polypeptide of interest; TEVp is the TEV protease variant according to the present invention; sTEV is the cleavage sequence of the TEV protease, which is EXXYXQG/S/H (SEQ ID NO: 30), wherein X is any amino acid residue, and preferably the cleavage sequence is selected from SEQ ID NOs: 7 and 8; preferably, wherein the polypeptide of interest is selected from ACTH, GLP-1/GLP-2, IFN-α, IFN-γ, Histatin, CCL5, SDF-1α, IGF-1, Leptin, BNP, Ex-4, preferably ACTH, preferably human ACTH, more preferably human ACTH of the amino acid sequence shown in SEQ ID NO: 2; preferably, wherein the protease variant and the cleavage sequence of the protease variant, such as the TEVp and the sTEV are connected directly or apart by one or more amino acid residues, provided that the protease variant such as the TEVp is capable of recognizing and cleaving the cleavage sequence of the protease variant, such as the sTEV; preferably, wherein the cleavage sequence of the protease variant, such as the sTEV and the Y1 are connected directly or apart by one or more amino acid residues, provided that the protease variant such as the TEVp is capable of recognizing and cleaving the cleavage sequence of the protease variant, such as the sTEV, preferably the cleavage sequence of the protease variant, such as the sTEV and Y1 being directly connected; preferably the fusion protein further comprises a tag, preferably wherein the tag is a purification tag; preferably the tag is selected from the group consisting of His tag, maltose binding protein (MBP) tag, glutathione transferase (GST) tag, NusA tag, SUMO tag, Avi tag, T7 tag, S tag, Flag tag, HA tag, c-myc tag, or Strep II tag; preferably, wherein the tag is at the N-terminus and/or C-terminus of the fusion protein, or there is no tag at the N-terminus of TEVp.

The present invention provides a polynucleotide sequence encoding the protease variant or the fusion protein, preferably selected from SEQ ID NOs: 14-16.

The present invention provides a polynucleotide construct comprising the polynucleotide sequence of the present invention.

The present invention provides an expression vector comprising the polynucleotide sequence according to the present invention or the polynucleotide construct according to the present invention. Preferably, the expression vector is a eukaryotic expression vector or a prokaryotic expression vector; preferably selected from the group consisting of pRS314, pYES2, baculovirus-S2 expression system and pcDNA3.1, or preferably selected from the group consisting of pET series expression vectors, pQE series expression vectors and pBAD series expression vectors.

The present invention provides a cell comprising the polynucleotide sequence according to the present invention, the polynucleotide construct according to the present invention, or the expression vector according to the present invention; preferably a eukaryotic cell or a prokaryotic cell; preferably the eukaryotic cell is selected from the group consisting of *Saccharomyces cerevisiae* and insect cell expression system; preferably the prokaryotic cell is selected from the group consisting of BL21, BL21 (DE3), BL21 (DE3) pLysS, Rosetta2, Rosetta2 pLysS, Tuner (DE3), or Origami 2.

The present invention provides a method of preparing the protease variant, preferably the TEV protease variant, according to the present invention, which comprises:
(1) culturing the cells in a medium under conditions suitable for culturing the cells of the present invention;
(2) harvesting the medium, or lysing the cells to harvest the lysate;
(3) purifying and obtaining the protease variant, preferably the TEV protease variant.

The present invention provides use of the protease variant according to the present invention, preferably the TEV protease variant for preparing a polypeptide of interest, wherein the protease variant, preferably the TEV protease variant, and the polypeptide of interest are expressed as a fusion protein, and preferably, said fusion protein is the fusion protein of the present invention.

The present invention provides a method for preparing a polypeptide of interest, which comprises:
(1) culturing the fusion protein of the present invention in a medium under suitable conditions;
(2) obtaining inclusion bodies of the fusion protein;
(3) dissolving inclusion bodies under high denaturation conditions, such as about 8 M urea or about 6 M guanidine hydrochloride;
(4) incubating under a moderate to high degree of denaturation conditions, under the condition of preferably 3 M-5 M urea, preferably 3.5 M-4.5 M urea, more preferably 4 M urea or 1 M-2 M guanidine hydrochloride, preferably 1.5 M guanidine hydrochloride at a certain temperature, such as 20-40° C., preferably 25° C. for a period of time, such as 10-24 hours, such as 12 hours;
(5) precipitating the protease variant, preferably the TEV protease after dilution with buffer such as Tris-HCl, preferably 50 mM Tris-HCl;
(6) removing the precipitate of the protease variant, preferably the precipitate of the TEV protease, by centrifugation to obtain the polypeptide of interest; and
(7) purifying the polypeptide of interest, preferably wherein the purification is performed by a technique selected from the group consisting of salting out, ultrafiltration, organic solvent precipitation, gel filtration, ion exchange chromatography column, reversed-phase high performance liquid chromatography.

Through the screening method of the present invention, the inventors have obtained new TEV protease variants 4D, 12D and 32C, indicating that a TEV protease variant that has a weak enzymatic cleavage activity of a TEV protease in a host and has an enzymatic cleavage activity of a TEV protease under extracellular denaturation conditions can be obtained by using the method of the present invention. In addition, when the TEV protease recognition sequence EXXYXQH (SEQ ID NO: 43) is used for screening, the TEV protease mutants that efficiently cleave ENLYFQ↓H (SEQ ID NO: 43) can also be obtained. The mutants are desirable for a number of polypeptides whose N-terminus starts with histidine.

1. The TEV protease variants of the present invention can be widely used to produce various polypeptides or proteins with natural N-terminus.

2. The TEV protease variants of the present invention are obtained through screening, but the mutant directly obtained cannot meet the requirements or partially meet the requirements. Through a series of combinations of mutation points, it is possible to obtain improved mutants with unique obtained properties further improved, such as the combination of L111F and other mutation(s). The TEV protease variants are characterized by no or extremely low intracellular activity, but a higher activity under moderate extracellular denaturation conditions.

3. The method of the present invention adopts DNA recombination technology and prokaryotic expression system to express the target protein, and has wide applicability.

4. Compared with the method of extracting ACTH from the porcine pituitary gland, the production cost of using the method of the present invention to prepare the human or pig derived ACTH can be hundreds of times lower than that of traditional production technology with porcine brain extraction, which greatly shortens the production cycle, saves production time and cost, and no longer depends on a large number of pig slaughter to obtain porcine pituitary glands, avoiding the risk of immunogenic allergic reactions caused by the use of the pig-derived ACTH, and greatly improving the safety of the medicine. In addition, ACTH prepared by the method is exactly the same as ACTH secreted by the human body, which has extremely high accuracy of the amino acid sequence and purity of the product, and an excellent biological activity, improving drug efficacy and reducing occurrence of adverse reactions. Compared with the method of the chemical organic synthesis, the present method has significantly reduced the difficulty and cost of preparation of the full-length human derived ACTH. With simple operation, no need for expensive catalysts and high-pressure equipment, and high yield, the present method is suitable for large-scale production. In general, the production process of this method is clear and simple, has good repeatability, is easy to realize large-scale production, and reduces environmental pollution.

DETAILED DESCRIPTION

Figure 1:
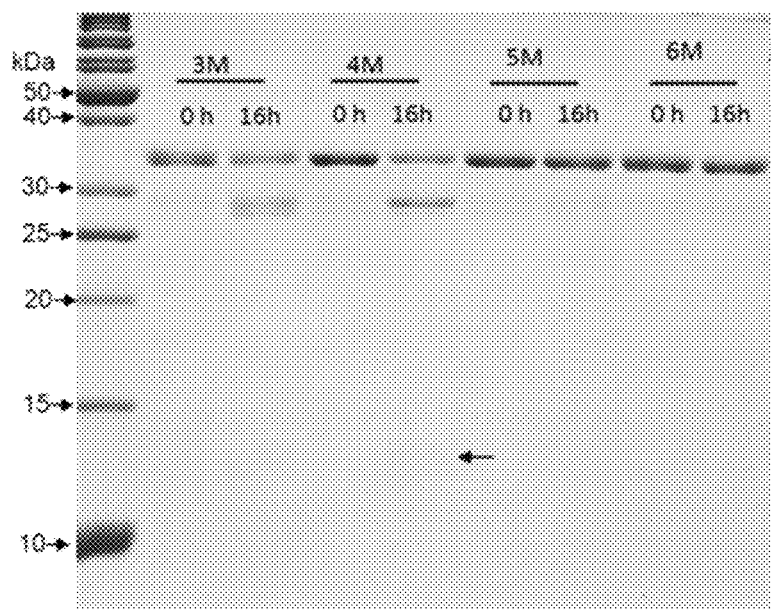
FIG. 1: SDS-PAGE gel Coomassie brilliant blue staining image of the digestion efficiency of the TEVP mutant 12D in different concentrations of urea. The arrow indicates the target protein.

In order to make the objectives, technical solutions and advantages of the present invention clearer, the embodiments of the present invention will be described in further detail below, but the embodiments of the present invention are not limited thereto.

As used herein, the term "host" can be any eukaryotic or prokaryotic cell suitable for expressing proteins. In one embodiment, the host cell is an *E. coli* cell.

As used herein, the term "extracellular denaturation conditions" refers to conditions under which the fusion protein containing the TEV protease is solubilized to have an enzymatic cleavage activity, for example, under the condition of 3 M-5 M urea, preferably 3.5 M-4.5 M urea, more preferably 4 M urea or 1 M-2 M guanidine hydrochloride, preferably 1.5 M guanidine hydrochloride.

As used herein, the TEV protease is a 27 kDa active domain in the N1a protease derived from tobacco etch virus (TEV). The S219V TEV protease with the amino acid sequence as shown in SEQ ID NO: 10 is used herein as the starting TEV protease. However, those skilled in the art should understand that various other TEV proteases can be used as the starting TEV protease in the method of the present invention. The TEV protease has strong site specificity and can recognize the seven-amino acid sequence of EXXYXQ (G/S) (SEQ ID NO: 9 or 11). The most common sequence is Glu-Asn-Leu-Tyr-Phe-Gln-Gly (or ENLYFQG) (SEQ ID NO: 29) with a cleavage site between glutamine Gln (P1) and glycine Gly (P1') (i.e., between P1 and P1'), the sequence specificity of which is far higher than that of proteases such as thrombin, factor Xa, and enterokinase.

As used herein, "TEV protease variant" refers to a TEV protease that has amino acid residue differences compared to the starting TEV protease used in the screening, wherein the variant does not imply that the TEV protease has a specific sequence and/or structure.

As used herein, "enzymatic cleavage activity of the TEV protease" refers to the enzymatic cleavage activity of the TEV protease to self-cleave a fusion protein comprising the TEV protease and its cleavage site. In one embodiment, the enzymatic cleavage activity of the TEV protease of the present invention is the activity for cleavage of the fusion protein comprising EXXYXQ (G/S/H) (SEQ ID NO: 30).

Herein, the fusion protein is displayed using a phage display technique. The phage display technique is a biotechnology in which the DNA sequence of the foreign protein or polypeptide is inserted into the appropriate position of the structural genes of the phage coat protein, such that the foreign gene is expressed with the expression of the coat protein and the foreign protein is displayed on the surface of the phage as the phage is reassembled. Those skilled in the art should understand that those skilled in the art can select other libraries of TEV protease random mutations to perform the methods of the present invention.

The phage display system can be a single-stranded filamentous phage display system, a lambda phage display system, and a T4 phage display system. In the case of a single-stranded filamentous phage display system, it may be a PIII display system and a PVIII display system. In the case of a lambda phage display system, it may be a PV display system and a D protein display system. Preferably, in one embodiment, the phage display system is a PIII display system.

As used herein, "moiety A" and "moiety B" refer to a pair of binding partners, for example selected from biotin, antibody, antigen, hapten, polystreptavidin, ligand, receptor, nucleic acid, enzyme, substrate and aptamer, provided that "moiety A" and "moiety B" specifically bind to each other.

In one embodiment, a solid support containing a moiety B is used to capture the fusion protein containing a moiety A. In one embodiment, when the tag is a biotin moiety, the solid support may be streptavidin-coated beads or resin, such as Dynabeads M-280 streptavidin, Dynabeads MyOne streptavidin, Dynabeads M-270 streptavidin (Invitrogen), streptavidin sepharose resin (Pierce), streptavidin hyper-linked resin, MagnaBind streptavidin beads (ThermoFisher Scientific), BioMag streptavidin, ProMag streptavidin, Silica streptavidin (Bangs Laboratories), Streptavidin Sepharose High Performance (GE Healthcare), streptavidin polystyrene microspheres (Microspheres-Nanospheres), streptavidin-coated polystyrene particles (Spherotech), or any other streptavidin-coated beads or resin commonly used by those skilled in the art to capture biotin-labeled molecules.

In one embodiment, the TEV protease can be displayed at the terminus (N-terminus) of the phage PIII protein in the form of Avi-TEVp-sTEV-Y1-PIII, wherein the Avi tag is a short peptide tag composed of 15 amino acid residues GLNDIFEAQKIEWHE (SEQ ID NO: 35). During the host expression process, Avi-TEVp-sTEV-Y1-PIII is biotinylated through the Avi tag.

As used herein, "enterokinase" is a heterodimeric serine protease that exists in the duodenum of mammals. The restriction site of the enterokinase is well known, such as DDDDK, and the nucleotide sequence and amino acid sequence of the enterokinase are also available to those skilled in the art, such as GenBank: AAC50138.1, AAB40026.1 and so on.

TEV Protease

Although TEV protease is often used to efficiently cleave fusion proteins, cleavage occurs only when both of them are soluble. At present, most polypeptide drugs are poor in solubility and are usually expressed in the form of inclusion bodies, which does not match the digestion conditions of TEV protease. Inclusion bodies need to be dissolved with high concentrations of urea or guanidine hydrochloride, but under these conditions, digestion is extremely challenging. It is difficult for the conventional TEV protease to have both efficient cleavage activity and simultaneous dissolution under the same conditions as a substrate.

Inclusion bodies facilitate purification, and the relatively pure target protein can be obtained by simple processing. However, the inclusion body protein needs to be dissolved with high concentrations of urea or guanidine hydrochloride. Under such conditions, the wild-type TEV protease is inactive or extremely low in activity and cannot efficiently cleave the fusion protein. At present, there are a large number of reports on improved TEV proteases, but the best conditions for digestion are physiological or non-denaturing conditions. Usually, they have a certain degree of tolerance to low-concentration denaturants (urea or guanidine hydrochloride), but most inclusion body proteins are insoluble under low-concentration denaturation conditions. Therefore, the conventional TEV protease is not suitable for this occasion.

The inventors found that the ideal production conditions for preparing polypeptide drugs by fusion of TEV proteases and polypeptides are: (1) the fusion protein is expressed in the form of inclusion bodies, which facilitates purification; (2) the fusion protein does not self-cleave in the cell, otherwise it is not conducive to purification; (3) after dissolution in a high-concentration denaturant, the fusion protein is diluted into an enzyme digestion reaction system containing moderate to high concentrations of denaturants, and at this time, the TEV protease recovers its activity and efficiently self-cleave to release polypeptides; and (4) the TEV protease variant that is screened and evolved from the high-capacity TEV protease library has a broad spectrum of amino acids at the P1' position of the its restriction site, so that it can be widely used to produce various polypeptides or proteins with natural N-termini.

The structure of a self-cleaving fusion protein that is usually prepared is provided in US2010035300A1. In the preparation of the fusion protein, the His tag is required to be closely connected to the target protein (for example, EGFP) to be expressed. The reason for this is that when the fusion protein is expressed in cells, the traditional wild-type TEVp or mutant TEVp has a certain enzymatic cleavage activity in the cell and self-cleavage occurs. EGFP after cleavage can be recovered through the His tag closely connected to it. Without the His tag, it is difficult to recover the protein because of premature self-cleavage in the cell, and EGFP cannot be efficiently produced. But this also brings about a problem, that is, the His tag of EGFP may have to be further removed according to specific needs. This is obviously more time-consuming and laborious.

In the present invention, the target protein in the fusion protein may not contain a tag, such as His. In one embodiment, the fusion protein comprises the structure of Avi-TEVp-sTEV-ACTH, wherein Avi is an Avi tag protein, and sTEV is a TEV protease restriction site. Since the TEVp variant (such as 12D variant) has an extremely low intracellular enzymatic activity, the expressed fusion protein will not be lysed in the cell basically. When the inclusion bodies are collected, dissolved with 8 M urea, and the environment is adjusted to 4 M urea, 12D exerts its enzymatic activity and then cleaves its recognition site as sTEV. After digestion, the final concentration of urea or guanidine hydrochloride is reduced to 0.5 M by simple dilution. The TEV proteases are easy to precipitate due to poor solubility and the released polypeptides with a biological activity are often easy to dissolve in the buffer, so that highly purified peptides can be obtained by centrifugation, which ingeniously removes the need for additional protease removal steps, and greatly simplifies the later purification process.

The formation of inclusion bodies is more conducive to purification: 1) it is easy to harvest highly concentrated and relatively pure protein by centrifugation; and 2) the inclusion bodies protect the protein from protease hydrolysis. In addition, the toxic protein is expressed in the form of inactive inclusion bodies and will not affect the growth of the host bacteria. For example, the TEV-ACTH fusion protein involved in this method is expressed in the form of inclusion bodies, which greatly simplifies the purification steps, can reach a higher concentration and purity, and is not subject to protease hydrolysis, so it is easy to obtain a stable high yield.

The Screening Method of the Present Invention

In the present invention, a large-capacity phage library of TEV random mutations is constructed, the key gene structure of which is Avi-TEV-sTEV-Y1-PIII. That is, the protease is displayed at the terminus of the phage PIII protein in such manner. The Avi tag is a short peptide tag composed of 15 amino acid residues (GLNDIFEAQKIEWHE, SEQ ID NO: 35), which can be linked to a biotin at the lysine residue (K) by a biotin ligase intracellularly or extracellularly to achieve biotinylation of the protein, and the biotinylated protein can be specifically bound by streptavidin. Based on these two reactions, the TEV phage of the present invention can be biotinylated intracellularly, and the biotinylated phage library can be immobilized with streptavidin magnetic beads. Under ideal conditions, the TEV variants with enzymatic cleavage activity when expressed in cells will be self-cleaved during the expression process, resulting in the final assembled phage PIII protein with only polypeptide Y1 at the terminus, without the Avi tag, which thus cannot be captured by magnetic beads. The TEV variants that have no enzymatic cleavage activity when expressed in cells will not undergo self-cleavage during the expression process, and the terminus of the final assembled phage PIII protein is Avi-TEV-sTEV-Y1, wherein the N-terminal Avi tag is biotinylated and can be captured by magnetic beads containing streptavidin. The phages captured by the magnetic beads are incubated in a moderate to high concentration of urea. The phage that undergoes enzymatic cleavage under such conditions will fall off the magnetic beads due to self-cleavage and enter the solution. The solution is collected to obtain the initial target phage, which can then enter the next round of screening after expansion. After several rounds of screening, the TEV protease variants that have a weak enzymatic cleavage in cells and have an enzymatic cleavage under extracellular denaturation conditions will be enriched. The enriched sequence is obtained through gene sequencing analysis, which can be verified one by one after cloning into the expression vector, thereby the TEV variant of the present invention is screened.

Determination of Activity or Efficiency of Enzymatic Cleavage

The enzymatic cleavage activity can be calculated according to the results of SDS-PAGE gel. Specifically, the inclusion bodies of the TEV protease variant are diluted 10 times and then 5×SDS loading buffer containing 10% β-mercaptoethanol is added. The sample is boiled at 100° C. for 5 minutes, and is loaded to run a gel. After the end, the gel is put in a Coomassie Brilliant Blue staining solution for staining for 30 minutes, then is put into a Coomassie Brilliant Blue Decolorizing Solution, and heated to decolorize for about 20 minutes until the background is colorless. Then, the gel is put into the gel imaging system to take pictures. The acquired pictures are processed with Image J software to quantify the gray value of the band. Intracelluar enzymatic cleavage activity=1-gray value of the fusion protein band/(gray value of the fusion protein band+gray value of Avi-TEV band*molecular weight of fusion protein/molecular weight of Avi-TEV).

Herein, the method of analyzing the gray value of electrophoretic bands with Image J software is the current general method.

Herein, the calculation method of extracellular digestion efficiency is as follows:

Extracellular digestion efficiency=1−the gray value of the fusion protein band after digestion/the gray value of the fusion protein band before digestion.

Herein, 8 M or more urea or 6 M or more guanidine hydrochloride is regarded as a high concentration of denaturant, and 4 M urea is a medium concentration of denaturant. The moderate-to-high degree of denaturation conditions refer to 4 M urea or 1.5 M guanidine hydrochloride, 50 mM Tris-HCl (pH8.0), 1 mM EDTA, 2 mM DTT, and the reaction temperature is 4° C.-37° C., preferably 25° C.

The following examples are provided to illustrate the invention.

EXAMPLES

Example 1: Acquisition of TEV Protease Variants

1. Construction of a Large-Capacity TEV Protease Random Mutation Library 1.1 Experimental Materials:

Escherichia coli TG1: supE hsd Δ5thiΔ (lac-proAB) F' [traD36proAB+lacIq lacZΔM15], purchased from Bioviewshine Bio Technology Co., Ltd. The phagemid vector pHEN1 (purchased from BioVector NTCC plasmid vector strain cell gene collection center, catalog number Biovector786623). DNA polymerase, T4 DNA ligase and restriction endonuclease were purchased from Invitrogen Trading Co., Ltd. The plasmid extraction kit and agarose gel DNA recovery kit were purchased from Tiangen Biotech (Beijing) Co., Ltd. Random Mutagenesis Kit (GeneMorph II Random Mutagenesis Kit) was purchased from Agilent Technologies. The primer synthesis and gene sequencing were completed in Nanjing Genscript Biotech Corporation.

1.2 Construction of a TEVP Random Mutation Library 1.2.1 Preparation of a TEVP DNA Fragment by Random Mutation PCR A large-scale random mutation of the TEVP S219V gene was performed with Random Mutagenesis Kit (GeneMorph II Random Mutagenesis Kit) with pQE30-TEV (S219V) (This 27 kDa TEV NIa protease variant gene was synthesized by Nanjing Genscript and cloned between BamH1 and HindIII of the pQE30 vector. The amino acid sequence of S219V is shown in SEQ ID NO: 10, and the nucleotide sequence is shown in SEQ ID NO: 3) as a template. The PCR primers are:

TEV-F:
5-AATCTCGAGGGATCTAAAGGTCCTGGAGAAAGCTTGTTTAAGGGACCA
C -3

TEV-R:
5- AATGGATCCTTGCGAGTACACCAATTC -3

The specific steps were operated according to the instructions of the kit, the number of PCR cycles and the amount of template were well controlled, and the PCR conditions were set to conditions that produce moderate degree of mutations. The 50 ul reaction system was prepared as follows: addition of 41.5 μl ddH2O, 5 μl 10× Mutazyme II reaction buffer, 1 μl 40 mM dNTP mixture (final concentration of 200 μM each), 0.5 μl mixture of primers (each primer of 250 ng/μl), 1 μl Mutazyme II DNA polymerase (2.5 U/μl), 1 μl the TEVP template (template amount of 10 ng) in sequence. PCR amplification conditions were: 95° C. pre-denaturation for 3 min; a total of 32 cycles of 95° C., 30 s; 60° C., 30 s; 72° C., 50 s, and final extension at 72° C. for 10 min. After the end of PCR, 5 ul product was taken to run 1% agarose gel for electrophoresis detection with the 1.1-kb gel standard in the kit as molecular weight standard. After staining, the brightness of the target band was compared with the standard to calculate the yield of PCR, which was divided by the amount of template to result in the amplification factor, which can be used to calculate the d value in the PCR process (calculation formula: $2^d$=PCR yield/initial template amount). The final d value of the TEVP random mutation PCR of the present invention is 7.5, and the corresponding mutation frequency is about 9 mutations/kb (refer to the instructions), which meets the expectation. The PCR product was extracted and purified with phenol chloroform, and then double digested with Xho1 and BamH1, and the digested product was recovered using agarose gel DNA recovery kit and stored at −20° C.

1.2.2 Preparation of a Linearized Vector

Figure 7:
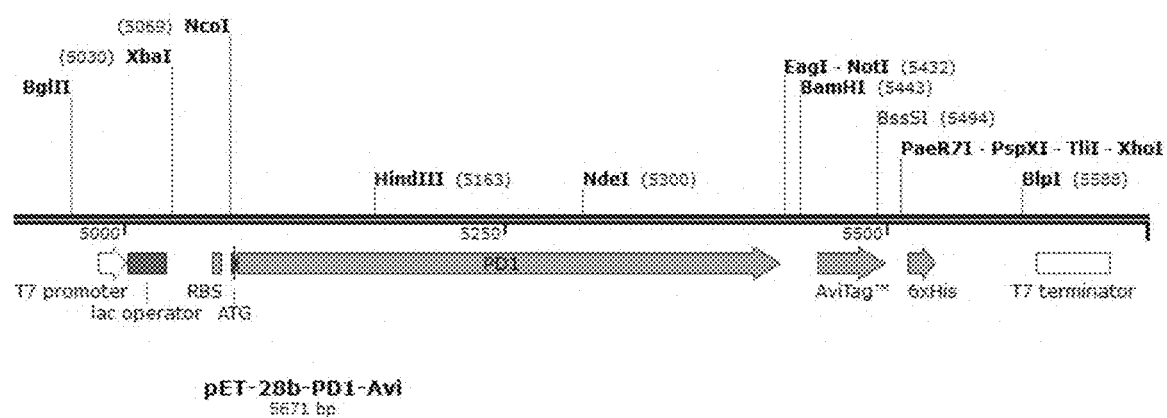
FIG. 7: Map of plasmid pET-28b-PD1-Avi.

Before linearizing the phagemid vector pHEN1 (purchased from the BioVector NTCC plasmid vector strain cell gene collection center, catalog number Biovector786623), it was modified first. First, an Avi tag sequence GLNDIFEAQKIEWHE (SEQ ID NO: 35) was inserted downstream of the signal peptide, and the resulting fusion protein can be biotinylated and then immobilized by streptavidin magnetic beads. pET28b-PD1-Avi (synthesized in Nanjing Genscript, gene structure of Nco1-PD1 gene-Not1-BamHI-GGGS linker-avi tag-Xho1, the PD1 gene is under Genebank accession number NM_005018, and the plasmid map shown in FIG. 7) was used as a template for PCR amplification of Avi tag, and PCR primers were as follows:

Avi-F: 5- ACTCCATGGCCGGTCTGAATGATATTTTTGAAGC -3

Avi-R: 5- AATCTCGAGCTCGTGCCACTCGATTTTCTG -3

Figure 8:
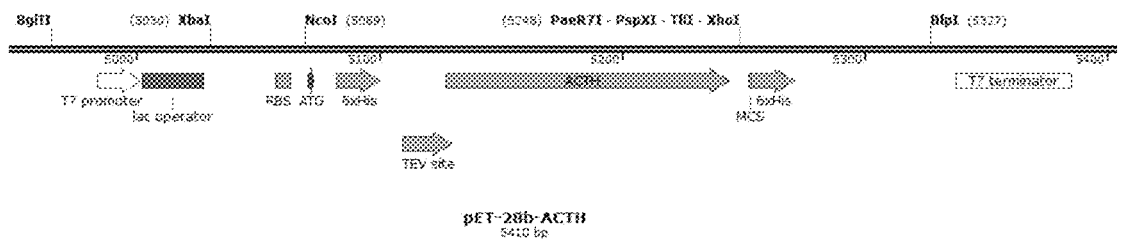
FIG. 8: Map of plasmid pET-28b-ACTH.

The product was purified by phenol chloroform, double digested with Nco1 and Xho1, and after the gel was recovered, it was ligated to the pHEN1 vector that had been digested with the same enzymes to obtain pHEN1-Avi. Then, a tandem sequence containing sTEV (nucleotide sequence: GAAAATCTGTATTTTCAGAGC (SEQ ID NO: 36), amino acid sequence: ENLYFQS (SEQ ID NO: 7)) and a human ACTH gene was inserted behind the Avi tag (cloning site Xho1+Not1), and the template for PCR amplification of sTEV-ACTH tandem sequence is pET28b-ACTH (synthesized in Nanjing Genscript, the plasmid map shown in FIG. 8, the amino acid sequence shown in SEQ ID NO: 2; the nucleotide sequence shown in SEQ ID NO: 13), and the PCR primers were as follows:

ACTH-F:
AATCTCGAGGGATCTGGATCCGGAGGTGGCGGTAGCGAAAATCTGTATTT
TCAGAGCTATAGCATGGAAC -3

ACTH-R:
5- AATGCGGCCGCAAATTCCAGCGGAAATGC -3

A BamH1 site was additionally introduced upstream of the primer, and the PCR product was purified by phenol chloroform, digested with Not1 and Xho1, and then ligated to the same digested pHEN1-Avi vector to obtain pHEN1-Avi-sTEV-ACTH. Vector linearization: pHEN1-Avi-sTEV-ACTH was doubly digested with Xho1 and BamH1, and large fragments in the digested product were subjected to gel recovery, and stored at −20° C.

1.2.3 Ligation and Recovery of Ligation Products

Figure 9:
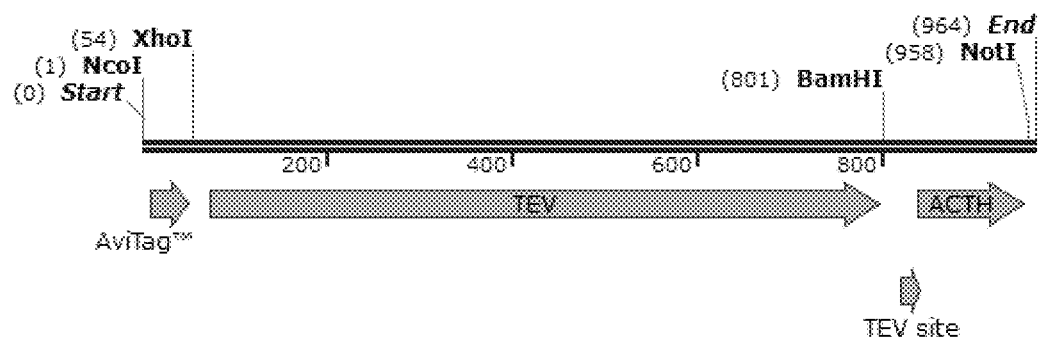
FIG. 9: Gene structure diagram of plasmid Avi-TEV-sTEV-ACTH.

The digested and recovered vector (pHEN1-Avi-sTEV-ACTH) was ligated with the insert fragment (randomly mutated TEVP gene) at 1:3, 1:5, 1:10. Specifically, the vector pHEN1-Avi-sTEV-ACTH was first prepared (see 1.2.2 Preparation of a linearized vector), then the insert fragment was prepared (see 1.2.1 Preparation of a TEVP DNA fragment by random mutation PCR), and the two are ligated by T4 DNA ligase (Thermo Fisher Scientific) to obtain pHEN1-Avi-TEVp-sTEV-ACTH. The ligation system was according to the instruction of the kit. Taking a 20 ul reaction system as an example: 150 ng of linearized vector, the corresponding amount of insert fragment (the molar ratio to the vector is 1:3 or 1:5 or 1:10), 10×T4 DNA Ligase buffer 2 ul, T4 DNA Ligase 1 ul were added in sequence to the PCR tube, and finally the volume was made up to 20 ul with ddH2O. By calculating the number of clones produced by transformation, the optimal ligation ratio was determined to be 1:5. The plasmid map is shown in FIG. 9. The optimal ligation ratio was determined to be 1:5. Different concentrations of ligation products were used for transformation to determine the optimal amount of transformation product to be 0.2 μg (10 μl). The ligation product was purified by phenol-chloroform extraction to remove protein and salt ions, and dissolved in ddH2O.

1.2.4 Electro-Transformation

The ligation product was transferred to the host bacteria TG1 by electroporation. The preparation method of competent cells for electro-transformation was in accordance with the Molecular Cloning Experiment Guide (third edition). 10 μl of ligation product was taken to be gently mixed with 200 μl of competent cells for electro-transformation, put in an ice bath for 2 min, and transferred to a pre-cooled electro-transformation cup with a gap of 0.2 cm for electro-transformation. The parameters of the electro-transformation instrument (Bio-Rad Gene-Pulser) were 2.5 KV, 25 μF, 200Ω. After the electric shock, 1 ml of SOC medium was immediately added, and aspirated out, followed by the electric shock cup was rinsed twice with 1 ml of SOC medium. 3 ml of bacterial solution was combined, and shaken for 45-60 min at 37° C., 200 rpm. The bacterial solution was diluted serially: $10^{-2}$, $10^{-3}$, and $10^{-4}$, with 100 ul bacterial cells taken for each gradient to spread small plates of SOC (containing 25 μg/ml carbenicillin), and the rest was centrifuged at 5000×g for 5 min to collect the bacterial cells, which was spread on square large plates (25×25 cm) of SOC (containing 25 μg/ml carbenicillin) after re-suspension. After incubation of the inverted plates at 37° C. for 12-16 h, count was performed on small plates. And the colonies on the large plates were rinsed with 2YT medium, gently scraped off with a spreading rod, divided into small tubes after adding glycerol to a final concentration of 50%, and frozen at −80° C. Calculation method of library capacity: the number of clones on the volume plate*the dilution factor*the total volume of the bacterial solution before dilution. The electro-transformation was repeated several times until the library capacity reaches $1×10^9$ or more.

1.2.5 Sequence Determination and Analysis

Several original bacterial clones were randomly picked, and the recombinant plasmid was verified by colony PCR. PCR verification primers are:

```
Forward primer:
5- CCACCATGGCCGGTCTGAATGATATTTTTGAAGC -3

Reverse primer:
5- TTGTTCTGCGGCCGCAAATTCCAGC -3
```

The PCR-positive recombinant plasmids were sent for sequencing (Genscript Biotechnology Co., Ltd.), and the randomness, library capacity and abundance of the constructed library were evaluated.

1.2.6 Evaluation of Library Capacity and Diversity

The molar ratio of the vector to the insert fragment was 1:5, and 10 μl of the ligation product was taken for electro-transformation. The transformation efficiency is $9×10^8$ cfu/μg DNA. After combining multiple transformations, the capacity is $2.02×10^9$, which meets the needs for screening. 20 clones were randomly picked from the peptide library and sequenced. The results show (Table 1) that the overall mutation frequency is moderate to low (1.5-7/kb). There is a certain deviation between the actual value and the theoretical value. One of the possible reasons is that the synonymous mutations are not counted, and the second is that the sample is small. As the number of sequencing samples increases, such deviation will gradually decrease. The above results show that the constructed TEVP random phage library meets the design requirements in terms of the basic framework, library capacity and diversity.

TABLE 1

Distribution of amino acid mutations in randomly picked clones

| Clone# | Site 1 | Site 2 | Site 3 | Site 4 | Site 5 |
|---|---|---|---|---|---|
| 1 | H46Q | I189M | S122T | N174Y | E188K |
| 2 | Y11H | T29A | | | |
| 3 | D10Y | | | | |
| 4 | Frameshift mutation | | | | |
| 5 | C130Y | Q197R | G213S | | |
| 6 | T29A | T43S | R50S | K229E | |
| 7 | I18F | F48S | Q58stop | | |
| 8 | G7E | S153G | | | |
| 9 | Frameshift mutation | | | | |
| 10 | No mutation | | | | |
| 11 | G53V | D148G | T175R | | |
| 12 | M87V | F186Y | V219A | | |
| 13 | H28Y | Q73stop | I138T | W198C | |
| 14 | E188A | | | | |
| 15 | S168T | | | | |
| 16 | F172S | M218L | | | |
| 17 | N176I | | | | |
| 18 | No mutation | | | | |
| 19 | No mutation | | | | |
| 20 | G62S | | | | |

2. Screening of Target Clones from a TEVP Random Mutation Phage Library 2.1 Experimental Materials The HRP-M13 antibody was purchased from Beijing Sino Biological Inc, and the 96-well ELISA plate and ELISA reagents were purchased from Sangon Biotech (Shanghai) Co., Ltd. Streptavidin magnetic beads were purchased from NEB. D-biotin, IPTG and other reagents were purchased from Sangon Biotech (Shanghai) Co., Ltd.

2.2 Culture of a Phage Library

At least one library volume of bacteria was taken and added to a 2 L Erlenmeyer flask containing 2×YT-CG (2×YT+100 μg/ml carbenicillin and 2% glucose), such that the initial OD600 value=about 0.1, and it was shaken at 37° C., 200 rpm until the OD600 reaches about 0.5. The helper phage M130K07 (purchased from Beijing Bio-viewshine Bio Technology Co., Ltd.) was added for infection (MOI=20), and incubation was continued at 37° C. for one hour with slow rotation at 100 rpm. Subsequently, the bacteria were collected by centrifugation (2000×g for 20 minutes), and the supernatant was removed and discarded as much as possible. The bacteria were resuspended with 1 L of 2×YT-CK (2×YT+100 μg/ml carbenicillin and 50 μg/ml kanamycin+200 μm D-biotin) and incubated overnight at 250 rpm at 25° C. The next day, the packaged phages were harvested and purified. The cell culture was transferred to a 750 ml centrifuge bottle and cooled slightly in ice. It was then centrifuged in a large bench top centrifuge at 4500 rpm for 30 minutes at 4° C. If the supernatant is turbid, it was transferred to another clean bottle and this step was repeated.

80% supernatant of the upper layer (do not stir the cell pellet) was transferred into another new 750 ml centrifuge bottle, and ⅙ volume of PEG/NaCl solution (20% [w/v] PEG-8000, 2.5 M NaCl) was added, mixed, then stood in ice for at least two hours, and was centrifuged at 4500 rpm for 30 minutes at 4° C. All of the supernatant was carefully removed, and 10 ml of PBS was added. The pellet was redissolved with a pipette and then transferred to a 2 ml EP tube. Centrifuge at 15000×g for 20 minutes at 4° C. to remove residual bacteria or debris. The supernatant was carefully pipetted into a new EP tube, to which ⅙ volume of PEG/NaCl solution was added, and it was placed on ice for 1 hour to precipitate the phage again, and then was centrifuged at 15000×g for 20 minutes at 4° C. to collect the phage precipitate. All supernatant was carefully aspirated and discarded. Subsequently, the phage precipitate was re-dissolved with an appropriate amount of PBS, and after complete dissolution, centrifuged at 15000×g for 10 minutes at 4° C. to remove the remaining insoluble impurities. The supernatant was dispensed into a new EP tube, 50% glycerin added, and stored at −80° C. for a long time.

2.3 Determination of Library Titer

According to the method of Carol MY Lee et al. (M Y Lee, Carol & Iorno, Niccoló & Sierro, Frederic & Christ, Daniel. (2007). Selection of human antibody fragments by phage display. Nature protocols. 2. 3001-8. 10.1038/nprot.2007.448), the phage library was diluted with 2×YT serially. 10 ul was taken for each of the dilutions of $10^{-9}$, $10^{-10}$, and $10^{-11}$, added to 200 ul of fresh TG1 bacterial solution that had been cultured to the logarithmic phase, mixed well, incubated at 37° C. for 30 minutes, and all spread on plates containing 2×YT-CG. The plates were incubated overnight at 30° C. in an incubator, the number of single colonies was counted the next day, and the titer was calculated.

2.4 Library Panning

The principle of panning TEVP variants of the present invention is as follows. Avi tag is a short peptide tag composed of 15 amino acid residues (GLNDIFEAQK-IEWHE, SEQ ID NO: 35), which can be ligated to biotin at a lysine residue by a biotin ligase both intracellularly and extracellularly, thereby realizing the biotinylation of the protein, and the biotinylated protein can be specifically bound by streptavidin. Based on these two reactions, the TEVp phage of the present invention can be biotinylated intracellularly, and the biotinylated phage library can be immobilized with streptavidin magnetic beads. Under ideal conditions, TEVP variants with enzymatic cleavage activity in the cell will be self-cleaved during the expression process, resulting in the final assembled phage PIII protein with only ACTH at the end and without Avi tag, and thus cannot be captured by magnetic beads. However, when expressed in cells, TEVP variants without enzymatic cleavage activity will not undergo self-cleavage during the expression process. The terminus of the final assembled phage PIII protein is Avi-TEVP-sTEV-ACTH, and the N-terminal Avi tag is biotinylated. Thus, they can be captured by magnetic beads containing streptavidin. The phage captured by the magnetic beads is incubated in moderate and high concentrations of urea. The TEVP variant, which is insoluble under physiological conditions, can dissolve and recover its activity under this condition, and undergo digestion. Phage that undergoes digestion under this condition will fall off the magnetic beads due to self-cleavage and enter the solution. The solution is collected to obtain the initial target phage, which can be amplified followed by the next round of screening. After several rounds of screening, TEV protease variants that have weak intracellular enzymatic cleavage activity and have enzymatic cleavage activity under extracellular denaturation conditions will be enriched. Through gene sequencing analysis, the enriched sequence is obtained, which can be verified one by one after cloning into an expression vector. The panning result of each round is shown in Table 2 below.

TABLE 2

Data of each round of panning

| Round | Input phage (pfu) | Recovered phage (pfu) | Recovery rate |
|---|---|---|---|
| 1 | $2.8 \times 10^{11}$ | $6.2 \times 10^{6}$ | $2.2 \times 10^{-5}$ |
| 2 | $2.0 \times 10^{11}$ | $2.8 \times 10^{7}$ | $1.1 \times 10^{-4}$ |
| 3 | $1.4 \times 10^{11}$ | $5.9 \times 10^{7}$ | $4.2 \times 10^{-4}$ |

The specific process of phage panning is as follows:

(1) Phage immobilization: In a clean 2 ml EP tube, the 100× library capacity of phage was diluted into the TBST buffer (50 mM Tris-HCl PH 7.5, 150 mM NaCl, 0.1% [v/v] Tween-20), mixed with an appropriate amount of streptavidin magnetic beads added, rotated at 4° C. and incubated for 20 min. The magnetic beads were precipitated with a magnet, and then washed with TBST 5 times to remove unbound phages.

(2) Screening for digestion: The TBS buffer containing 3 M urea was added to the magnetic beads, and incubated for 1-2 h at room temperature. The magnetic beads were precipitated with a magnet, and all the supernatant was collected as much as possible.

(3) Phage amplification: The eluted phage was added to 50 ml of TG1 host bacteria with OD600=0.5, and shaken slowly at 37° C. for 1 hour. 100 μg/ml carbenicillin and 2% glucose were added, and continued to incubate for 2 hours. The helper phage (M130K07 (purchased from Beijing Bioviewshine Bio Technology Co., Ltd.)) was added for infection (MOI=20), and incubation was continued at 37° C. for one hour with slow rotation. Subsequently, the bacteria were collected by centrifugation, and the supernatant was removed and discarded as much as possible. The bacteria were resuspended with 100 ml of 2×YT-CK (2×YT+100 μg/ml carbenicillin and 50 μg/ml kanamycin+200 μm D-biotin) and incubated overnight at 250 rpm at 25° C. The next day, the packaged phages were harvested and purified. The culture was transferred to a clean 50 ml centrifuge tube and centrifuged at 13,000 g at 4° C. for 20 min. 80% supernatant of the upper layer was transferred into a fresh centrifuge tube, and ⅙ volume of PEG/NaCl solution was added, and precipitated at 4° C. for more than 1 hour. Then it was centrifuged again to collect the precipitate, and appropriate amount of PBS was added to resuspend the phage precipitate, which was centrifuged again to remove bacterial debris and other impurities. The supernatant was collected, to which ⅙ volume of PEG/NaCl solution was added, stood on ice for 1 hour, and was then centrifuged again to collect the precipitate, which was dissolved in an appropriate amount of PBS. Then it was centrifuged at 13,000 g for 10 minutes to remove insoluble impurities, and the supernatant was transferred to another fresh EP tube, which was the eluate after amplification.

(4) 1 μl of purified phage was taken for titer determination, and the others were used for the next round of panning or storage.

(5) Analysis of enrichment of screened sequences by sequencing: After 3 rounds of panning, the phage eluted from the last round was used to infect the host bacteria and plated on a 2×YT-CG plate and incubated at 30° C. overnight. On the next day, single-clone colonies are picked, subjected to colony PCR to identify whether they belong to the library sequence, and the positive clones were sent for sequencing analysis. By analyzing the sequencing results and counting the frequency of mutation sites, the best 7 mutants were finally selected as candidate clones.

3. Characterization of Candidate Clones

The above seven candidate sequences were digested (Nco1/Not1) and cloned into the expression vector pET28b (purchased from Novagen), and transferred into Rosetta2 (DE3) (purchased from Hunan Youbio) for expression. Expression conditions are as follows. The cells were cultured in LB medium at 37° C. until OD600-around 0.6. Induction conditions are as follows: shaking at 250 rpm at 37° C., 2 mM IPTG induction for 4 hours. Bacteria treatment: centrifugation to collect bacteria, resuspend the bacteria and disrupt the bacterial cells by ultrasound, centrifugation to collect the precipitate of inclusion bodies, washing the inclusion bodies, and finally dissolving the inclusion bodies with 8 M urea (50 mM Tris-HCl, 1 mM EDTA, 2 mM DTT, 8 M urea, pH 8.0).

Inclusion body protein dilution and digestion test: The inclusion body protein of each candidate clone was diluted with TEVP digestion buffer (50 mM Tris-HCl, 1 mM EDTA, 2 mM DTT, pH 8.0) to make the final concentration of urea to be 3 M or 4 M, and then digested at 25° C. overnight. The next day, the SDS-PAGE gel was run to check the digestion. The protein electrophoresis bands were processed by Image J software, and the gray values of the bands were calculated.

Optimization of digestion conditions: The positive clones obtained through the above digestion test should be further tested for digestion efficiency under different conditions. These conditions include: different urea concentrations, different temperatures, different guanidine hydrochloride concentrations, DTT and EDTA concentrations in the reaction solution.

Through the above screening, the present invention finally results in 3 mutants with weak intracellular enzymatic cleavage activity but normal extracellular activity. The test results are shown in FIGS. 1, 2, 3 and 4A-B.

Specific process: Each TEV protease variant-ACTH fusion protein that had been dissolved in 8 M urea buffer was added to the diluent at a ratio of 1:10, and the diluent was 50 mM Tris-HCl pH8.0, 1 mM EDTA, 2 mM DTT containing different concentrations of urea. When the final concentration of urea was 4 M, the diluent was 3.56 M Urea, 50 mM Tris-HCl pH8.0, 1 mM EDTA, 2 mM DTT. After mixing each sample, it was immediately divided into two EP tubes, into one of which is added 5×SDS loading buffer and the sample was boiled at 100° C. for 5 minutes. This was the sample for digestion for 0 h. The other was placed at 25° C. for self-digestion for 16 h, and then 5×SDS loading buffer was added, and the sample was boiled at 100° C. for 5 min. This was the sample for digestion for 16 h. Subsequently, the SDS-PAGE denaturing gel was run to detect the samples of the variants each digested for 0 h and 16 h. After the electrophoresis, the gel was stained with Coomassie brilliant blue, decolorized, and photographed. The pictures were processed with the Image J software to calculate the gray value of the electrophoretic band. The calculation method is as follows:

Intracellular digestion activity=1−the gray value of the fusion protein band before digestion/(the gray value of the fusion protein band before digestion+the gray value of the Avi-TEVP band x fusion protein molecular weight/Avi-TEVP molecular weight).

Extracellular digestion efficiency=1−the gray value of the fusion protein band after digestion/the gray value of the fusion protein band before digestion.

As shown in Table 3, the digestion activity of 4D, 12D and 32C protease variants decreased significantly in cells, and the extracellular cleavage efficiencies in 4 M urea were all above 30%. The variant of TEV protease used in the preparation of ACTH polypeptide of the present invention is any one in Table 3. The TEV protease variants screened in the present invention can be used for the preparation of other recombinant polypeptides and proteins.

Table 3: The yield of fusion protein of several protease variants and ACTH (calculation method: run SDS-PAGE denaturing gel with the fusion protein sample together with BSA standard product, stain with Coomassie Brilliant Blue staining solution after running the gel, then transfer the gel in the decolorizing solution to remove the background and take a picture. Compare the gray value of the BSA standard band in the picture with the gray value of the sample to estimate the concentration of the sample, and then calculate concentration and yield of the fusion protein), intracellular activity and extracellular tolerance to 4 M urea (using S219V as control), based on comparison of protein band gray values. The data are the statistical results of the yield of the fusion proteins of the TEVP variants expressed in three different batches, and the ratio of intracellular and extracellular digestion.

TABLE 3

The yield of fusion protein of several protease variants and ACTH (calculation method: run SDS-PAGE denaturing gel with the fusion protein sample together with BSA standard product, stain with Coomassie Brilliant Blue staining solution after running the gel, then transfer the gel in the decolorizing solution to remove the background and take a picture. Compare the gray value of the BSA standard band in the picture with the gray value of the sample to estimate the concentration of the sample, and then calculate concentration and yield of the fusion protein), intracellular activity and extracellular tolerance to 4M urea (using S219V as control), based on comparison of protein band gray values. The data are the statistical results of the yield of the fusion proteins of the TEVP variants expressed in three different batches, and the ratio of intracellular and extracellular digestion.

| Clone name | Yield of fusion protein (mg/L) | Ratio of intracellular digestion (%) | Ratio of extracellular digestion (%) |
| --- | --- | --- | --- |
| 4D | 220.92 ± 6.93 | 10.75 ± 4.40 | 52.93 ± 11.27 |
| 12D | 185.73 ± 9.26 | 1.49 ± 1.10 | 61.07 ± 14.65 |
| 32C | 237.78 ± 11.02 | 2.48 ± 0.51 | 26.89 ± 2.95 |
| S219V | 88.39 ± 6.89 | 71.97 ± 8.08 | 70.96 ± 6.23 |

Note:
The yield of the fusion protein here refers to the fusion protein that has not been digested. The digested fusion protein in cells is not counted because it is of no use value. S219V is a mutant having the amino acid mutation at position 219 of the wild-type TEVP from serine (S) to valine (V);
4D: The amino acid at position 111 of S219V is mutated from leucine (L) to phenylalanine (F), and the amino acid at position 138 is mutated from isoleucine (I) to lysine (K);
12D: The amino acid at position 28 of S219V is mutated from histidine (H) to leucine (L), the amino acid at position 111 is mutated from leucine (L) to phenylalanine (F), and the amino acid at position 196 is mutated from glutamic acid (Q) to histidine (H);
32C: The amino acid at position 111 of S219V is mutated from leucine (L) to histidine (H), the amino acid at position 135 is mutated from serine (S) to glycine (G); and the amino acid at position 187 is mutated from methionine (M) to isoleucine (I).

Figure 2:
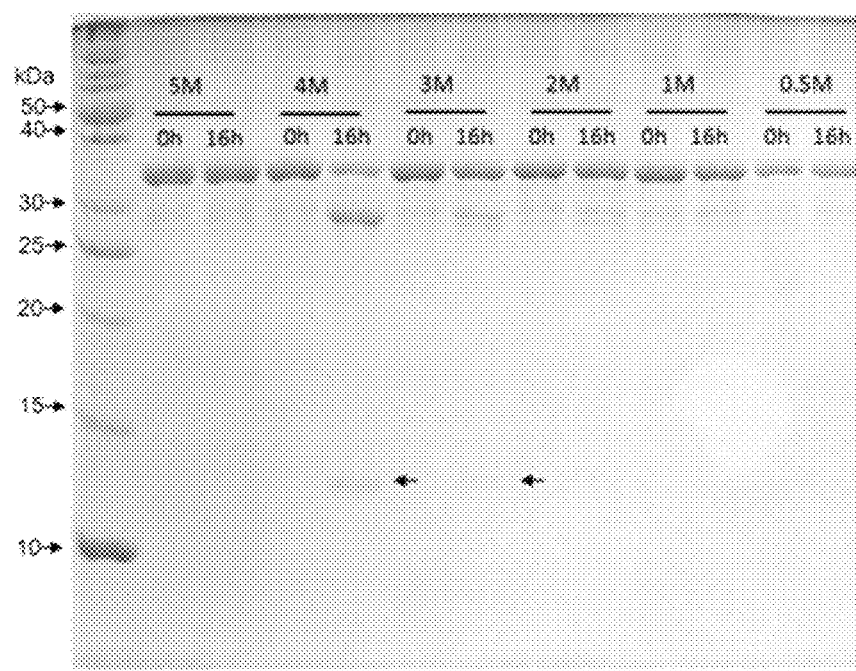
FIG. 2: SDS-PAGE gel Coomassie brilliant blue staining image of the digestion efficiency of the TEVP mutant 4D in different concentrations of urea. The arrow indicates the target protein.
Figure 3:
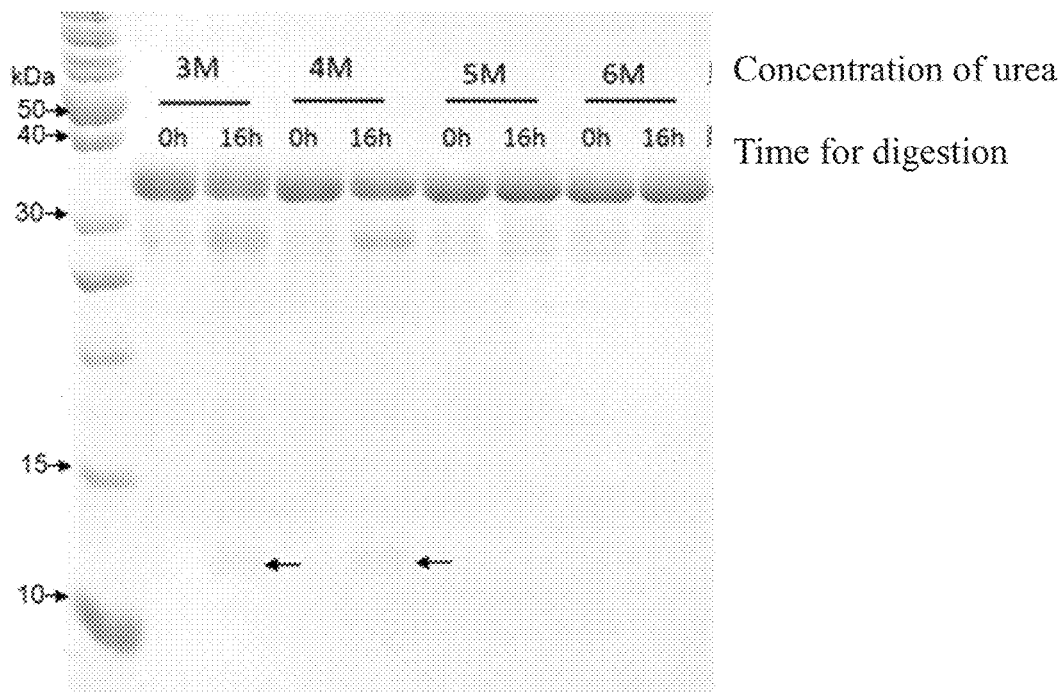
FIG. 3: SDS-PAGE gel Coomassie brilliant blue staining image of the digestion efficiency of the TEVP mutant 32C in different concentrations of urea. The arrow indicates the target protein.
Figure 4A:
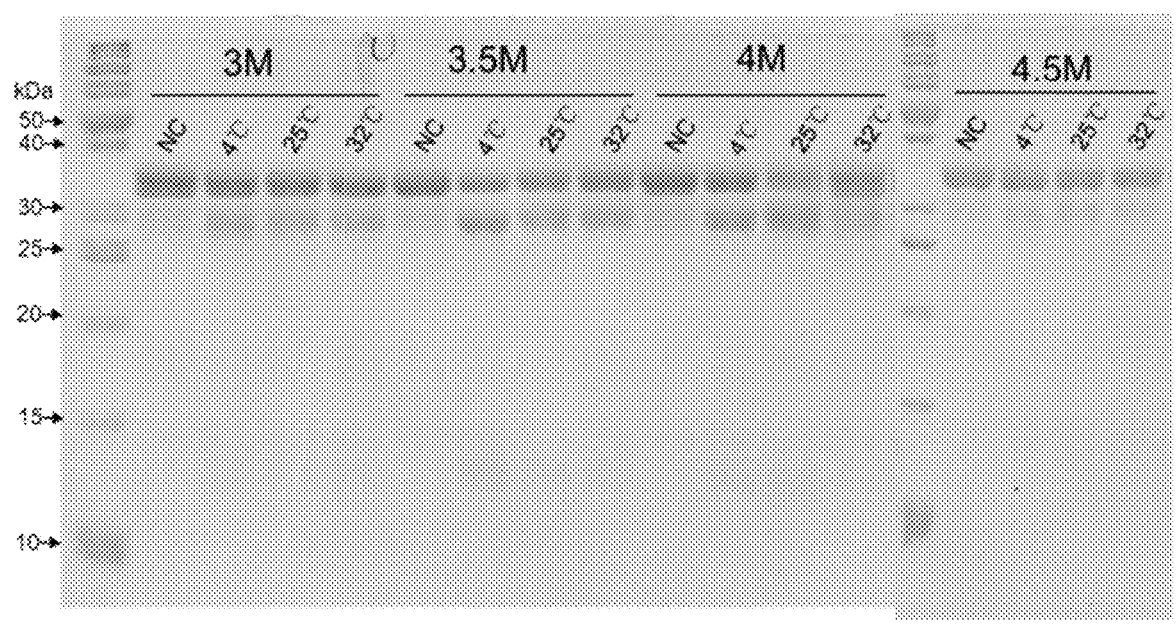
FIG. 4A: SDS-PAGE gel Coomassie brilliant blue staining image of the digestion efficiency of the TEVP mutant 4D in different concentrations of urea.
Figure 4B:
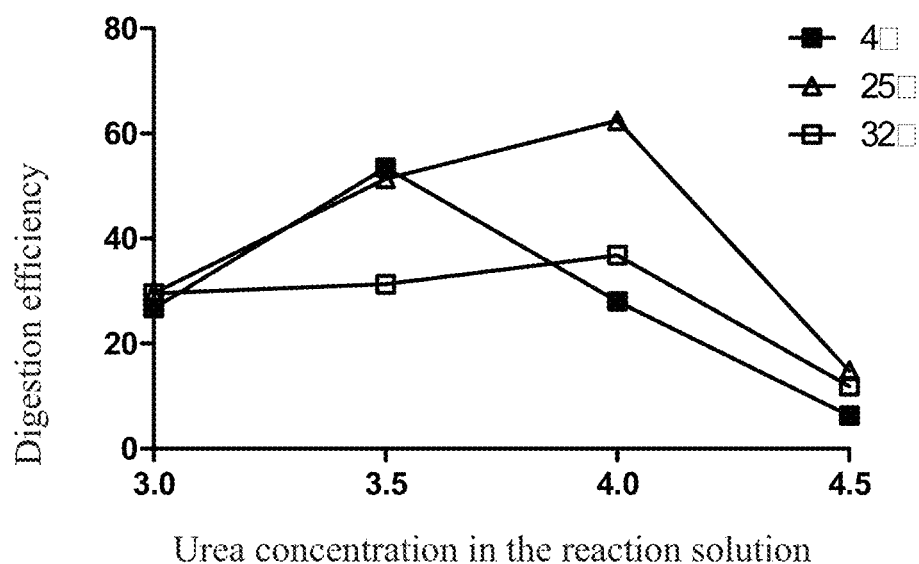
FIG. 4B: Comparison of gray values of electrophoretic bands.

FIG. 1 shows that TEVp mutant 12D has the highest digestion efficiency in 4 M urea solution; FIG. 2 shows that TEVp mutant 4D has the highest digestion efficiency in 4 M urea; FIG. 3 shows that TEVp mutant 32C has the highest digestion efficiency in 4 M urea; and FIGS. 4A and 4B show that TEVp variant 4D has the highest digestion efficiency under the conditions of 4 M urea and 25° C. When the urea concentration exceeds 4 M, the digestion efficiency of various mutants gradually decreases.

Figure 5:
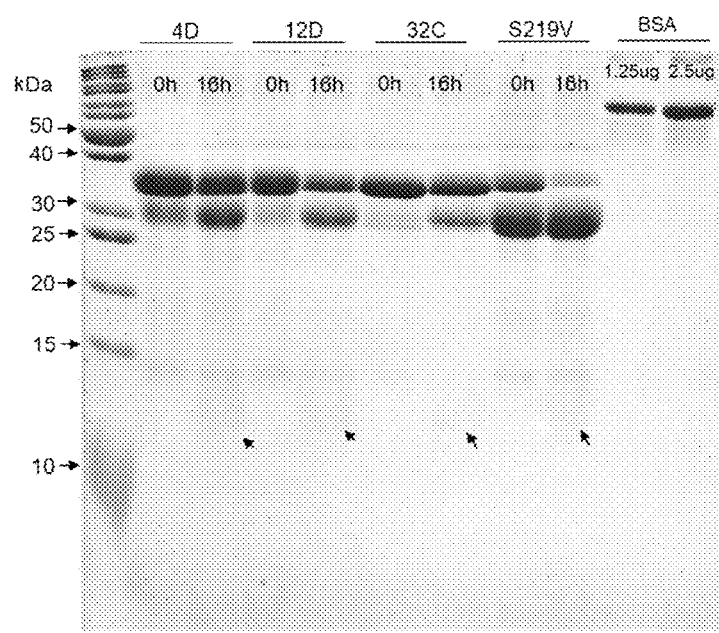
FIG. 5: Comparison of the intracellular and extracellular digestion activities of the TEVP mutants 4D, 12D and 32C with those of S219V. The arrow indicates the target protein.

FIG. 5 shows that the intracellular digestion activity of TEVp mutants 4D, 12D and 32C screened by the present invention is significantly lower than that of the S219V control (based on the 0 hour band comparison), and the extracellular digestion activity is slightly less than or equal to that of S219V.

Figure 6:
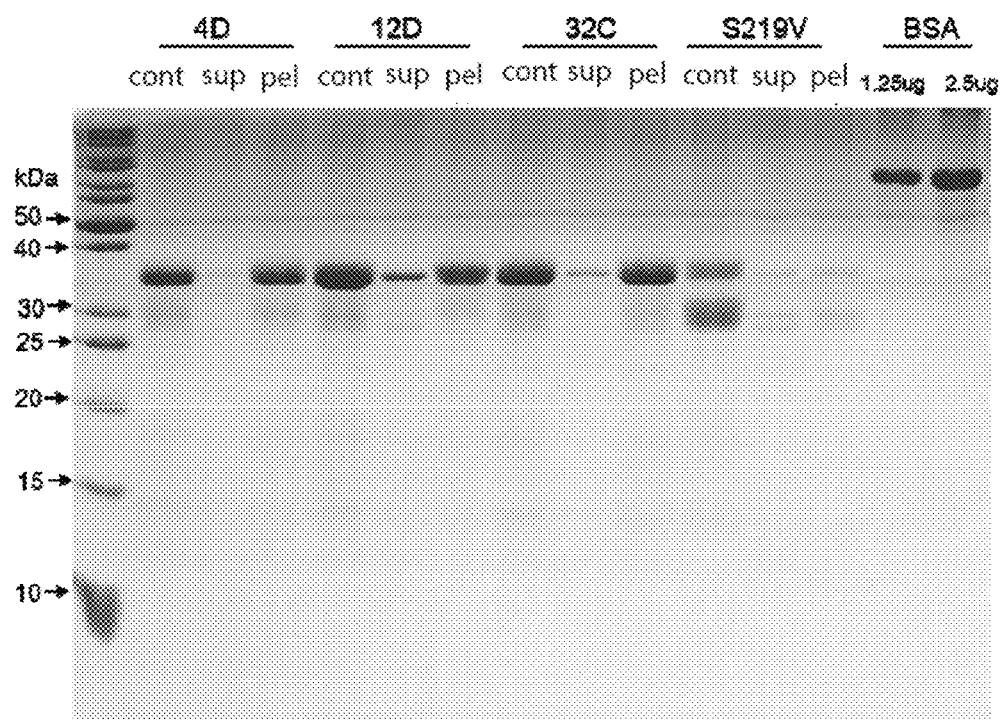
FIG. 6: The solubility test of fusion proteins of the TEVP mutants 4D, 12D, 32C and S219V in 0.5M urea.

FIG. 6 shows that the solubility of fusion protein of each TEVp mutant in 0.5 M urea is low (there was only a small amount of protein in the diluted supernatant, most of the protein was in the diluted precipitate), which demonstrates that the fusion protein of the TEVP mutant existed as a precipitate after being diluted to 0.5 M urea.

The TEV protease mutant used in the preparation of the ACTH polypeptide of the present invention is any one in Table 1. The TEV protease mutant screened in the present invention can be used for the preparation of other recombinant polypeptides and proteins.

Example 2: Preparation of ACTH Polypeptide by the TEVP-ACTH Fusion Protein

1. Construction of the TEVP-ACTH Fusion Protein Expression Vector

In Example 1, the carboxyl end of ACTH released by digestion of fusion protein had a His tag, which was required to be removed in actual production. Therefore, it was necessary to introduce a stop codon downstream of the ACTH gene by PCR. Specifically, the Avi-TEVP-sTEV-ACTH region in the open reading frame of the vector was amplified by PCR using the plasmid with TEV protease variant 12D that had the best effect in step 3 of Example 1 as a template (the sequence of TEVP variant 12D is SEQ ID NO: 5, and the sequence of ACTH gene is SEQ ID NO: 13). Amplification was performed with KOD-plus DNA high-fidelity polymerase (Toyobo), and the amplification procedure was: 95° C. pre-denaturation for 2 min, and 30 cycles of amplification of 98° C. denaturation for 10 s, 60° C. annealing for 30 s, 68° C. extension for 1 min 12 s). A stop codon was introduced downstream of the gene. The primers were as follows:

```
TEV-ACTH-F:
5- CCACCATGGCCGGTCTGAATGATATTTTTGAAGC -3

TEV-ACTH -R:
5- AGAGCGGCCGCTTATTAAAATTCCAGCGGAAATGCTTCTGC -3
```

The underlined parts were the restriction sites Nco1 and Not1, respectively. The PCR product and the vector pET-28b (Novagen) were digested with Nco1 and Not1 at 37° C. for 3 hours, and the digested fragments were recovered by the gel, and then ligated with T4 DNA ligase at 20° C. for 2 hours. The ligation product was transformed into DH5a competent cells, and then the transformed product was spread on a kanamycin-resistant (50 μg/ml) LB plate and cultured until a single colony emerged. The single colony was picked and the plasmid was extracted for digestion verification. The recombinant plasmid was sent to Genscript for sequencing to obtain the plasmid pET-28b-Avi-TEVP-sTEV-ACTH (the sTEV sequence therein is in the TEVP-ACTH plasmid).

2. Inducible Expression, Purification, Digestion and Verification of the TEVP-ACTH Fusion Protein The constructed expression vector was transformed. Specifically, 50 ng plasmid pET-28b-TEVP-sTEV-ACTH was added to the corresponding chemically competent cell Rosetta2 (DE3), put in an ice bath for 30 minutes, heated shock at 42° C. for 45 seconds, put in an ice bath for 2 minutes, and 1 ml of LB medium without antibiotics was added, cultured for 1 hour at 37° C. 100 ul of bacterial solution was taken to be spread on an LB plate containing kanamycin (50 μg/ml)+chloramphenicol (34 μg/ml), and incubated at 37° C. until a single colony grew out.

Inducible expression of the TEVP-ACTH fusion protein: A single colony was picked and cultured in LB liquid medium containing kanamycin (50 μg/ml) and chloramphenicol (34 μg/ml) until OD600=0.5-0.8. The culture was inoculated into LB liquid medium at a volume ratio of 1:50, cultured with vigorous shaking at 37° C. to OD600=0.5-0.8, and induced with IPTG at a final concentration of 2 mM at 37° C. for 4 h. During the expression process, the TEVP-ACTH fusion protein exists as insoluble inclusion bodies. After the fermentation was completed, the cells were collected and ultrasonically disrupted, and washed with a washing buffer (composition: 50 mM Tris-HCl, 200 mM NaCl, 10 mM EDTA, 10 mM β-Mercaptoethanol, 0.5% Triton X-100) several times to obtain the crude extract of the TEVP-ACTH fusion protein, to which a buffer solution containing denaturing agent guanidine hydrochloride or urea (composition: 50 mM Tris-HCl pH 8.0, 1 mM EDTA, 2 mM DTT, 8 M Urea or 6 M GuHCl) to dissolve TEVP-ACTH fusion protein to prepare a denaturing solution.

The fusion protein denaturation solution was diluted ten times with TEVP digestion buffer (3.556 M Urea, 50 mM Tris-HCl, 1 mM EDTA, 2 mM DTT, pH 8.0) to allow the final concentration of urea to be 4 M, and stood at 25° C. for self-cleavage overnight. After the digested product was diluted 8 times (the diluent was 50 mM Tris-HCl pH 8.0), TEV protease and uncleaved fusion protein precipitated out due to poor solubility (see FIG. 6), and ACTH polypeptide can be dissolved into the solution. Therefore, the ACTH stock solution was obtained after the supernatant was collected after 30 minutes of centrifugation at 13000 g at low temperature and high speed at 4° C.

3. Purification and Storage of ACTH

ACTH stock solution was filtered with a 0.22 μm filter membrane to filter impurities, concentrated with a 1k ultrafiltration centrifuge tube (Millipore) while desalting, and then precipitated with 50% ammonium sulfate. ACTH formed a suspension on the upper layer of the solution, which was collected carefully and dissolved with PBS, concentrated and desalted by ultrafiltration to obtain a highly purified recombinant human or pig derived ACTH solution, which was then freeze-dried and stored.

4. Structural Identification of ACTH

Figure 10:
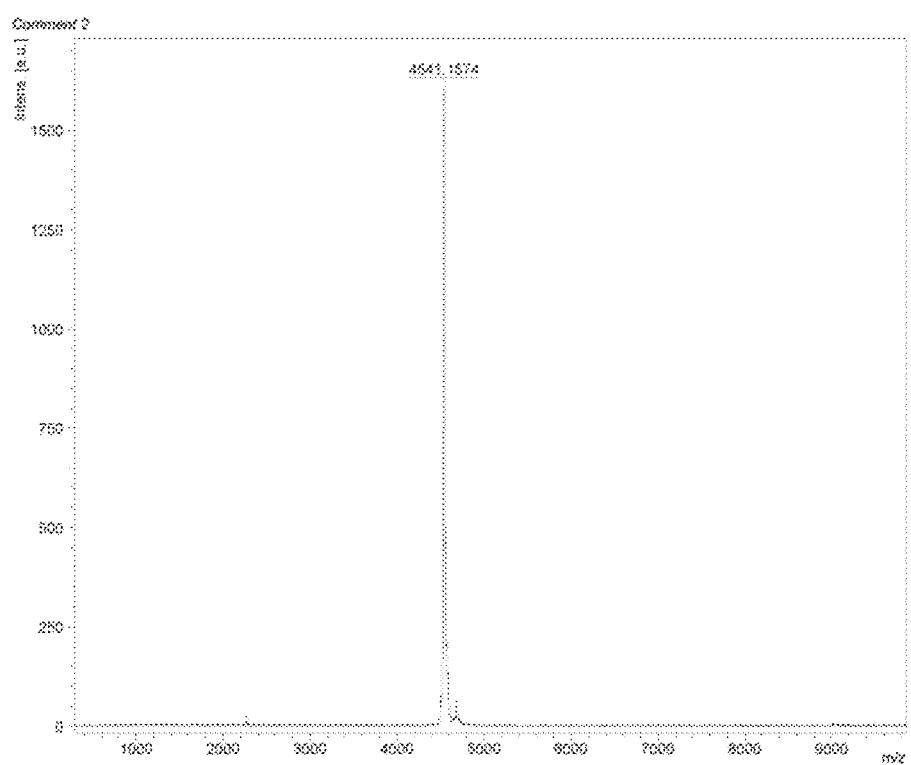
FIG. 10: Mass spectrometer determination of the molecular weight of purified ACTH.

The molecular weight of the purified ACTH was measured by a mass spectrometer, and the measured molecular weight was consistent with the theoretical value. The results are shown in FIG. 10.

5. Activity Determination of ACTH

Healthy 2-week-old SD rats were anesthetized with 1% sodium pentobarbital (40 mg/kg), and the adrenal glands were removed under aseptic conditions. The capsule and medulla were removed and put into Hanks balanced salt solution. After cut into 1 mm³ pieces, they were transferred to the digestion solution containing type I collagenase and DNase for digestion for 1 hour while shaking at 5 minutes intervals. The cells were mechanically separated by pipetting using a pipette several times to form a suspension, which was then filtered with a cell sieve into a 50 ml centrifuge tube and centrifuged at 1000×g for 10 minutes. The supernatant was carefully aspirated, and the precipitated cells were washed twice with Hanks solution, and finally resuspended in DMEM/F12 medium (Gibco) containing 20% fetal bovine serum to adjust the concentration to 2×10⁵/ml. They were inoculated on 90 mm petri dishes, and incubated at 37° C., 5% CO2. The growth process and morphological changes of adrenal cells were observed under an inverted phase-contrast microscope. After 48 hours of culture, adrenal cells can be seen to grow adherently under the microscope, the cell volume increased, the cell body was round or polygonal, the cell body was large, the cytoplasm was transparent and there were many regular-sized particles in the cytoplasm. Thus, rat adrenal cortex cells were obtained.

Figure 11:
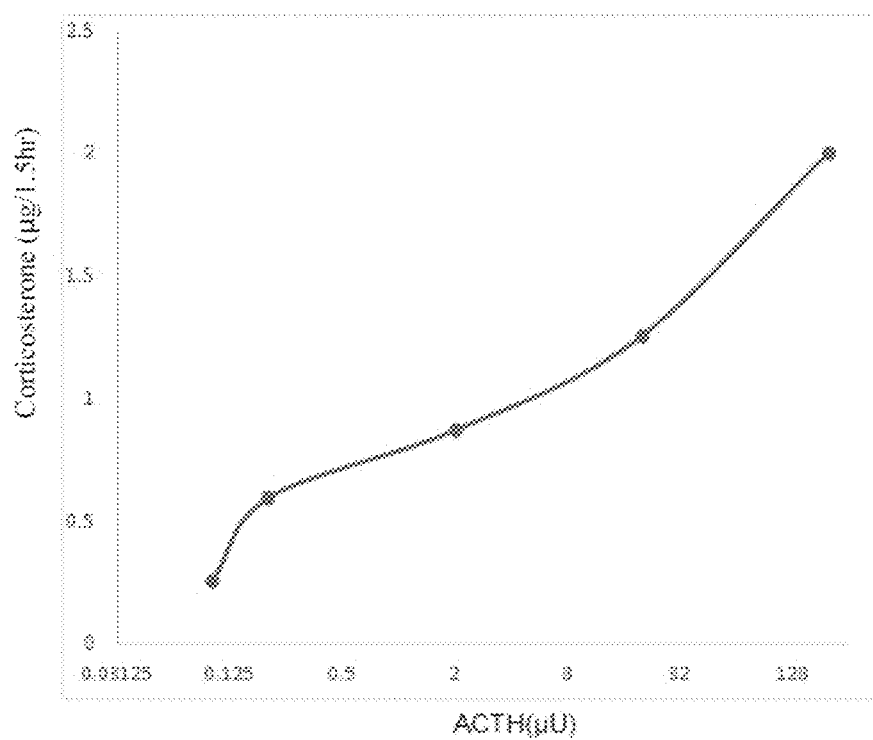
FIG. 11: The method for extracellular determination of ACTH activity.

The purified ACTH was incubated with rat adrenal cortex cells ex vivo. Specifically, different concentrations of ACTH (0.1 μU, 0.2 μU, 2 μU, 20 μU, 200 μU, 1 U=10 μg protein) were added to each group of adrenal cells (the volume ratio of cells to ACTH was 400:1). After incubation at 37° C. for 24 hours, the culture medium was taken and centrifuged to remove the cell debris, and the supernatant was then determined for corticosterone concentration by enzyme-linked immunoassay (for enzyme-linked immunoassay, please refer to He Shangjin et al. "The expression and significance of PCNA in rat adrenal cell culture." Clinical Urology Journal of Surgery 21.8 (2006): 625-626). The results show that as the concentration of ACTH increases, the concentration of corticosterone also gradually increases. ACTH stimulates cells to secrete steroid hormones, and the activity of ACTH is quantified by measuring the concentration of corticosterone produced (ELISA method). The results show that multiple batches of ACTH after purification have high biological activity and activity stability. The results are shown in FIG. 11.

The above are only preferred embodiments of the present invention, and do not limit the present invention in any form. Therefore, any simple modifications, equivalent changes and modifications made to the above embodiments based on the technical essence of the present invention without departing from the content of the technical solution of the present invention still fall within the scope of the technical solution of the present invention.

The invention claimed is:

1. A method for screening a protease variant comprising the following steps:
   (1) constructing a library of protease random mutations,
   (2) screening the library of protease random mutations for a protease variant that has a lower enzymatic cleavage activity of a protease in a host than an initial protease and retains the enzymatic cleavage activity of the initial protease under extracellular denaturation conditions; and
   wherein the initial protease is a S219V TEV protease having the amino acid sequence of SEQ ID NO: 10 or is an enterokinase, and the extracellular denaturation conditions are 3 M-5 M urea or 1 M-2 M guanidine hydrochloride,
   (3) the step of characterizing the protease variant.

2. The method according to claim 1, wherein the library of protease random mutations is a phage library of protease random mutations.

3. The method according to claim 1, wherein in step (1) random mutations are made with a suitable protease template to construct the library.

4. The method according to claim 1, wherein the TEV protease variant has a lower enzymatic cleavage activity in a host than the S219V protease having the amino acid sequence of SEQ ID NO: 10 and retains the enzymatic cleavage activity of the S219V protease having the amino acid sequence of SEQ ID NO: 10 under extracellular denaturation conditions.

5. The method according to claim 4, wherein the TEV protease is displayed at the terminus of the phage PIII protein in the form of Avi-TEVp-sTEV-Y1-PIII, wherein Avi tag is a short peptide tag composed of 15 amino acid residues GLNDIFEAQKIEWHE (SEQ ID NO: 35), wherein TEVp is a TEV protease, sTEV is the cleavage sequence of the TEV protease and Y1 is the protein of interest; wherein the cleavage sequence of the TEV protease is EXXYXQG/S/H (SEQ ID NO: 30), and wherein X is any amino acid residue.

6. The method according to claim 5, wherein the enzymatic cleavage activity is determined on TEVp-sTEV-Y1.

7. The method according to claim 5, wherein the screening comprises biotinylation of the phage library of the TEV protease random mutations in a host.

8. The method according to claim 7, wherein the screening comprises treating the biotinylated phage library with streptavidin magnetic beads, incubating the phage captured by the magnetic beads in a moderate to high concentration of urea for a period of time, and separating the magnetic beads from the solution containing the target phage.

9. The method according to claim 5, wherein Y1 is human or porcine ACTH or GLP-1.

10. The method according to claim 1, wherein the host is *E. coli*.

* * * * *

SEQUENCE LISTING

<160> NUMBER OF SEQ ID NOS: 43

<210> SEQ ID NO 1
<211> LENGTH: 242
<212> TYPE: PRT
<213> ORGANISM: Tobacco etch virus

<400> SEQUENCE: 1

```
Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Gly Leu Asn Ala Asp Ser
        195                 200                 205

Val Leu Trp Gly Gly His Lys Val Phe Met Ser Lys Pro Glu Glu Pro
```

```
                210               215               220
Phe Gln Pro Val Lys Glu Ala Thr Gln Leu Met Asn Glu Leu Val Tyr
225                 230                 235                 240

Ser Gln

<210> SEQ ID NO 2
<211> LENGTH: 39
<212> TYPE: PRT
<213> ORGANISM: Homo sapiens

<400> SEQUENCE: 2

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 3
<211> LENGTH: 726
<212> TYPE: DNA
<213> ORGANISM: Tobacco etch virus

<400> SEQUENCE: 3
ggagaaagct tgtttaaggg accacgtgat tacaacccga tatcgagcac catttgtcat      60
ttgacgaatg aatctgatgg gcacacaaca tcgttgtatg gtattggatt tggtcccttc    120
atcattacaa acaagcactt gtttagaaga ataatggaa cactgttggt ccaatcacta     180
catggtgtat tcaaggtcaa gaacaccacg actttgcaac aacacctcat tgatgggagg    240
gacatgataa ttattcgcat gcctaaggat ttcccaccat ttcctcaaaa gctgaaattt    300
agagagccac aaagggaaga gcgcatatgt cttgtgacaa ccaacttcca aactaagagc    360
atgtctagca tggtgtcaga cactagttgc acattcccctt catctgatgg catattctgg    420
aagcattgga ttcaaaccaa ggatgggcag tgtggcagtc cattagtatc aactagagat    480
gggttcattg ttggtataca ctcagcatcg aatttcacca acacaaacaa ttatttcaca    540
agcgtgccga aaacttcat ggaattgttg acaaatcagg aggcgcagca gtgggttagt     600
ggttggggat taaatgctga ctcagtattg tgggggggcc ataaagttttt catgttaaa    660 cctgaagagc cttttcagcc agttaaggaa gcgactcaac tcatgaatga attggtgtac    720
tcgcaa                                                              726

<210> SEQ ID NO 4
<211> LENGTH: 242
<212> TYPE: PRT
<213> ORGANISM: Artificial sequence
<220> FEATURE:
<223> OTHER INFORMATION: TEV protease mutant 4D

<400> SEQUENCE: 4

Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60
```

```
Lys Val Lys Asn Thr Thr Thr Leu Gln Gln His Leu Ile Asp Gly Arg
 65                  70                  75                  80

Asp Met Ile Ile Ile Arg Met Pro Lys Asp Phe Pro Phe Pro Gln
                 85                  90                  95

Lys Leu Lys Phe Arg Glu Pro Gln Arg Glu Glu Arg Ile Cys Phe Val
            100                 105                 110

Thr Thr Asn Phe Gln Thr Lys Ser Met Ser Ser Met Val Ser Asp Thr
            115                 120                 125

Ser Cys Thr Phe Pro Ser Ser Asp Gly Lys Phe Trp Lys His Trp Ile
130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
                180                 185                 190

Gln Glu Ala Gln Gln Trp Val Ser Gly Trp Gly Leu Asn Ala Asp Ser
            195                 200                 205

Val Leu Trp Gly Gly His Lys Val Phe Met Val Lys Pro Glu Glu Pro
210                 215                 220

Phe Gln Pro Val Lys Glu Ala Thr Gln Leu Met Asn Glu Leu Val Tyr
225                 230                 235                 240

Ser Gln

<210> SEQ ID NO 5
<211> LENGTH: 242
<212> TYPE: PRT
<213> ORGANISM: Artificial sequence
<220> FEATURE:
<223> OTHER INFORMATION: TEV protease mutant 12D

<400> SEQUENCE: 5

Gly Glu Ser Leu Phe Lys Gly Pro Arg Asp Tyr Asn Pro Ile Ser Ser
 1               5                  10                  15

Thr Ile Cys His Leu Thr Asn Glu Ser Asp Gly Leu Thr Thr Ser Leu
                20                  25                  30

Tyr Gly Ile Gly Phe Gly Pro Phe Ile Ile Thr Asn Lys His Leu Phe
            35                  40                  45

Arg Arg Asn Asn Gly Thr Leu Leu Val Gln Ser Leu His Gly Val Phe
50                  55                  60

Lys Val Lys Asn Thr Thr Thr Leu Gln Gln His Leu Ile Asp Gly Arg
 65                  70                  75                  80

Asp Met Ile Ile Ile Arg Met Pro Lys Asp Phe Pro Phe Pro Gln
                 85                  90                  95

Lys Leu Lys Phe Arg Glu Pro Gln Arg Glu Glu Arg Ile Cys Phe Val
            100                 105                 110

Thr Thr Asn Phe Gln Thr Lys Ser Met Ser Ser Met Val Ser Asp Thr
            115                 120                 125

Ser Cys Thr Phe Pro Ser Ser Asp Gly Ile Phe Trp Lys His Trp Ile
130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175
```

Asn Tyr Phe Thr Ser Val Pro Lys Asn Phe Met Glu Leu Leu Thr Asn
            180                 185                 190

Gln Glu Ala His Gln Trp Val Ser Gly Trp Gly Leu Asn Ala Asp Ser
        195                 200                 205

Val Leu Trp Gly Gly His Lys Val Phe Met Val Lys Pro Glu Glu Pro
    210                 215                 220

Phe Gln Pro Val Lys Glu Ala Thr Gln Leu Met Asn Glu Leu Val Tyr
225                 230                 235                 240

Ser Gln

<210> SEQ ID NO 6
<211> LENGTH: 242
<212> TYPE: PRT
<213> ORGANISM: Artificial sequence
<220> FEATURE:
<223> OTHER INFORMATION: TEV protease mutant 32C

<400> SEQUENCE: 6

Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys His Val
            100                 105                 110

Thr Thr Asn Phe Gln Thr Lys Ser Met Ser Ser Met Val Ser Asp Thr
        115                 120                 125

Ser Cys Thr Phe Pro Ser Gly Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Ile Glu Leu Leu Thr Asn
            180                 185                 190

Gln Glu Ala Gln Gln Trp Val Ser Gly Trp Gly Leu Asn Ala Asp Ser
        195                 200                 205

Val Leu Trp Gly Gly His Lys Val Phe Met Val Lys Pro Glu Glu Pro
    210                 215                 220

Phe Gln Pro Val Lys Glu Ala Thr Gln Leu Met Asn Glu Leu Val Tyr
225                 230                 235                 240

Ser Gln

<210> SEQ ID NO 7
<211> LENGTH: 7
<212> TYPE: PRT
<213> ORGANISM: Artificial sequence
<220> FEATURE:
<223> OTHER INFORMATION: TEV protease restriction site

```
<400> SEQUENCE: 7

Glu Asn Leu Tyr Phe Gln Ser
1               5

<210> SEQ ID NO 8
<211> LENGTH: 7
<212> TYPE: PRT
<213> ORGANISM: Artificial sequence
<220> FEATURE:
<223> OTHER INFORMATION: TEV protease restriction site

<400> SEQUENCE: 8

Glu Asn Leu Tyr Phe Gln His
1               5

<210> SEQ ID NO 9
<211> LENGTH: 7
<212> TYPE: PRT
<213> ORGANISM: Artificial sequence
<220> FEATURE:
<223> OTHER INFORMATION: TEV protease restriction site
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 9

Glu Xaa Xaa Tyr Xaa Gln Gly
1               5

<210> SEQ ID NO 10
<211> LENGTH: 242
<212> TYPE: PRT
<213> ORGANISM: Artificial sequence
<220> FEATURE:
<223> OTHER INFORMATION: TEV protease mutant S219V

<400> SEQUENCE: 10

Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
                20                  25                  30

Tyr Gly Ile Gly Phe Gly Pro Phe Ile Ile Thr Asn Lys His Leu Phe
            35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160
```

```
Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Gly Leu Asn Ala Asp Ser
        195                 200                 205

Val Leu Trp Gly Gly His Lys Val Phe Met Val Lys Pro Glu Glu Pro
    210                 215                 220

Phe Gln Pro Val Lys Glu Ala Thr Gln Leu Met Asn Glu Leu Val Tyr
225                 230                 235                 240

Ser Gln

<210> SEQ ID NO 11
<211> LENGTH: 7
<212> TYPE: PRT
<213> ORGANISM: Artificial sequence
<220> FEATURE:
<223> OTHER INFORMATION: TEV protease restriction site
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 11

Glu Xaa Xaa Tyr Xaa Gln Ser
1               5

<210> SEQ ID NO 12
<211> LENGTH: 21
<212> TYPE: DNA
<213> ORGANISM: Artificial sequence
<220> FEATURE:
<223> OTHER INFORMATION: TEVp restriction site

<400> SEQUENCE: 12
gaaaatctgt attttcagag c                                           21

<210> SEQ ID NO 13
<211> LENGTH: 117
<212> TYPE: DNA
<213> ORGANISM: Homo sapiens

<400> SEQUENCE: 13
agctatagca tggaacattt tcgttggggt aaaccggttg gtaaaaaacg tcgtccggtt    60
aaagtttatc cgaatggtgc agaagatgaa tcggcagaag catttccgct ggaattt      117

<210> SEQ ID NO 14
<211> LENGTH: 726
<212> TYPE: DNA
<213> ORGANISM: Artificial sequence
<220> FEATURE:
<223> OTHER INFORMATION: TEV protease mutant 4D

<400> SEQUENCE: 14
ggagaaagct tgtttaaggg accacgtgat acaacccga tatcgagcac catttgtcat     60
ttgacgaatg aatctgatgg gcacacaaca tcgttgtatg gtattggatt tggtcccttc   120
atcattacaa acaagcactt gtttagaaga ataatggaa cactgttggt ccaatcacta    180
catggtgtat tcaaggtcaa gaacaccacg actttgcaac aacacctcat tgatgggagg   240
```

```
gacatgataa ttattcgcat gcctaaggat ttcccaccat ttcctcaaaa gctgaaattt      300
agagagccac aaagggaaga gcgcatatgt tttgtgacaa ccaacttcca aactaagagc      360
atgtctagca tggtgtcaga cactagttgc acattcccct catctgatgg caaattctgg      420
aagcattgga ttcaaaccaa ggatgggcag tgtggcagtc cattagtatc aactagagat      480
gggttcattg ttggtataca ctcagcatcg aatttcacca acacaaacaa ttatttcaca      540
agcgtgccga aaacttcat ggaattgttg acaaatcagg aggcgcagca gtgggttagt       600
ggttggggat taaatgctga ctcagtattg tggggggggcc ataaagtttt catggttaaa    660
cctgaagagc cttttcagcc agttaaggaa gcgactcaac tcatgaatga attggtgtac     720
tcgcaa                                                                726

<210> SEQ ID NO 15
<211> LENGTH: 726
<212> TYPE: DNA
<213> ORGANISM: Artificial sequence
<220> FEATURE:
<223> OTHER INFORMATION: TEV protease mutant 12D

<400> SEQUENCE: 15
ggagaaagct tgtttaaggg accacgtgat tacaacccga tatcgagcac catttgtcat     60
ttgacgaatg aatctgatgg gctcacaaca tcgttgtatg gtattggatt tggtcccttc    120
atcattacaa acaagcactt gtttagaaga ataatggaa cactgttggt ccaatcacta      180
catggtgtat tcaaggtcaa gaacaccacg actttgcaac aacacctcat tgatgggagg    240
gacatgataa ttattcgcat gcctaaggat ttcccaccat ttcctcaaaa gctgaaattt    300
agagagccac aaagggaaga gcgcatatgt tttgtgacaa ccaacttcca aactaagagc    360
atgtctagca tggtgtcaga cactagttgc acattccctt catctgatgg catattctgg    420
aagcattgga ttcaaaccaa ggatgggcag tgtggcagtc cattagtatc aactagagat    480
gggttcattg ttggtataca ctcagcatcg aatttcacca acacaaacaa ttatttcaca    540
agcgtgccga aaacttcat ggaattgttg acaaatcagg aggcgcatca gtgggttagt     600
ggttggggat taaatgctga ctcagtattg tggggggggcc ataaagtttt catggttaaa  660
cctgaagagc cttttcagcc agttaaggaa gcgactcaac tcatgaatga attggtgtac    720
tcgcaa                                                                726

<210> SEQ ID NO 16
<211> LENGTH: 726
<212> TYPE: DNA
<213> ORGANISM: Artificial sequence
<220> FEATURE:
<223> OTHER INFORMATION: TEV protease mutant 32C

<400> SEQUENCE: 16
ggagaaagct tgtttaaggg accacgtgat tacaacccga tatcgagcac catttgtcat    60
ttgacgaatg aatctgatgg gcacacaaca tcgttgtatg gtattggatt tggtcccttc   120
atcattacaa acaagcactt gtttagaaga ataatggaa cactgttggt ccaatcacta     180
catggtgtat tcaaggtcaa gaacaccacg actttgcaac aacacctcat tgatgggagg    240
gacatgataa ttattcgcat gcctaaggat ttcccaccat ttcctcaaaa gctgaaattt   300
agagagccac aaagggaaga gcgcatatgt catgtgacaa ccaacttcca aactaagagc    360
atgtctagca tggtgtcaga cactagttgc acattccctt caggtgatgg catattctgg    420
```

```
aagcattgga ttcaaaccaa ggatgggcag tgtggcagtc cattagtatc aactagagat    480
gggttcattg ttggtataca ctcagcatcg aatttcacca acacaaacaa ttatttcact    540
agcgtgccga aaaacttcat tgaattgttg acaaatcagg aggcgcagca gtgggttagt    600
ggttggggat taaatgctga ctcagtattg tggggggggcc ataaagtttt catggttaaa    660
cctgaagagc cttttcagcc agttaaggaa gccactcaac tcatgaatga attggtgtac    720
tcgcaa                                                                726
```

```
<210> SEQ ID NO 17
<211> LENGTH: 7
<212> TYPE: PRT
<213> ORGANISM: Artificial Sequence
<220> FEATURE:
<223> OTHER INFORMATION: recognition site

<400> SEQUENCE: 17

Glu Asn Leu Tyr Phe Gln Gly
1               5
```

```
<210> SEQ ID NO 18
<211> LENGTH: 49
<212> TYPE: DNA
<213> ORGANISM: Artificial Sequence
<220> FEATURE:
<223> OTHER INFORMATION: TEV-F

<400> SEQUENCE: 18
aatctcgagg gatctaaagg tcctggagaa agcttgttta agggaccac                 49
```

```
<210> SEQ ID NO 19
<211> LENGTH: 27
<212> TYPE: DNA
<213> ORGANISM: Artificial Sequence
<220> FEATURE:
<223> OTHER INFORMATION: TEV-R

<400> SEQUENCE: 19
aatggatcct tgcgagtaca ccaattc                                         27
```

```
<210> SEQ ID NO 20
<211> LENGTH: 34
<212> TYPE: DNA
<213> ORGANISM: Artificial Sequence
<220> FEATURE:
<223> OTHER INFORMATION: Avi-F

<400> SEQUENCE: 20
actccatggc cggtctgaat gatattttg aagc                                  34
```

```
<210> SEQ ID NO 21
<211> LENGTH: 30
<212> TYPE: DNA
<213> ORGANISM: Artificial Sequence
<220> FEATURE:
<223> OTHER INFORMATION: Avi-R

<400> SEQUENCE: 21
aatctcgagc tcgtgccact cgattttctg                                      30
```

```
<210> SEQ ID NO 22
<211> LENGTH: 70
<212> TYPE: DNA
<213> ORGANISM: Artificial Sequence
<220> FEATURE:
```

<223> OTHER INFORMATION: ACTH-F

<400> SEQUENCE: 22
aatctcgagg gatctggatc cggaggtggc ggtagcgaaa atctgtattt tcagagctat    60
agcatggaac                                                          70

<210> SEQ ID NO 23
<211> LENGTH: 29
<212> TYPE: DNA
<213> ORGANISM: Artificial Sequence
<220> FEATURE:
<223> OTHER INFORMATION: ACTH-R

<400> SEQUENCE: 23
aatgcggccg caaattccag cggaaatgc                                     29

<210> SEQ ID NO 24
<211> LENGTH: 34
<212> TYPE: DNA
<213> ORGANISM: Artificial Sequence
<220> FEATURE:
<223> OTHER INFORMATION: Forward primer

<400> SEQUENCE: 24
ccaccatggc cggtctgaat gatattttg aagc                                34

<210> SEQ ID NO 25
<211> LENGTH: 25
<212> TYPE: DNA
<213> ORGANISM: Artificial Sequence
<220> FEATURE:
<223> OTHER INFORMATION: Reverse primer

<400> SEQUENCE: 25
ttgttctgcg gccgcaaatt ccagc                                         25

<210> SEQ ID NO 26
<211> LENGTH: 15
<212> TYPE: PRT
<213> ORGANISM: Artificial Sequence
<220> FEATURE:
<223> OTHER INFORMATION: tag

<400> SEQUENCE: 26

Gly Leu Asn Asp Ile Phe Glu Ala Gln Lys Ile Glu Trp His Glu
1               5                   10                  15

<210> SEQ ID NO 27
<211> LENGTH: 34
<212> TYPE: DNA
<213> ORGANISM: Artificial Sequence
<220> FEATURE:
<223> OTHER INFORMATION: TEV-ACTH-F

<400> SEQUENCE: 27
ccaccatggc cggtctgaat gatattttg aagc                                34

<210> SEQ ID NO 28
<211> LENGTH: 41
<212> TYPE: DNA
<213> ORGANISM: Artificial Sequence
<220> FEATURE:
<223> OTHER INFORMATION: TEV-ACTH -R

<400> SEQUENCE: 28

```
agagcggccg cttattaaaa ttccagcgga aatgcttctg c                      41
```

<210> SEQ ID NO 29
<211> LENGTH: 7
<212> TYPE: PRT
<213> ORGANISM: Artificial sequence
<220> FEATURE:
<223> OTHER INFORMATION: Synthetic construct

<400> SEQUENCE: 29

```
Glu Asn Leu Tyr Phe Gln Gly
1               5
```

<210> SEQ ID NO 30
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: VARIANT
<222> LOCATION: (2)..(3)
<223> OTHER INFORMATION: X is any amino acid residue
<220> FEATURE:
<221> NAME/KEY: VARIANT
<222> LOCATION: (5)..(5)
<223> OTHER INFORMATION: X is any amino acid residue
<220> FEATURE:
<221> NAME/KEY: VARIANT
<222> LOCATION: (7)..(7)
<223> OTHER INFORMATION: X is Gly, Ser, or His

<400> SEQUENCE: 30

```
Glu Xaa Xaa Tyr Xaa Gln Xaa
1               5
```

<210> SEQ ID NO 31
<211> LENGTH: 49
<212> TYPE: DNA
<213> ORGANISM: Artificial sequence
<220> FEATURE:
<223> OTHER INFORMATION: Synthetic construct

<400> SEQUENCE: 31

```
aatctcgagg gatctaaagg tcctggagaa agcttgttta agggaccac              49
```

<210> SEQ ID NO 32
<211> LENGTH: 27
<212> TYPE: DNA
<213> ORGANISM: Artificial sequence
<220> FEATURE:
<223> OTHER INFORMATION: Synthetic construct

<400> SEQUENCE: 32

```
aatggatcct tgcgagtaca ccaattc                                      27
```

<210> SEQ ID NO 33
<211> LENGTH: 34
<212> TYPE: DNA
<213> ORGANISM: Artificial sequence
<220> FEATURE:
<223> OTHER INFORMATION: Synthetic construct

<400> SEQUENCE: 33

```
actccatggc cggtctgaat gatatttttg aagc                              34
```

<210> SEQ ID NO 34
<211> LENGTH: 30

<212> TYPE: DNA
<213> ORGANISM: Artificial sequence
<220> FEATURE:
<223> OTHER INFORMATION: Synthetic construct

<400> SEQUENCE: 34
aatctcgagc tcgtgccact cgattttctg          30

<210> SEQ ID NO 35
<211> LENGTH: 15
<212> TYPE: PRT
<213> ORGANISM: Artificial sequence
<220> FEATURE:
<223> OTHER INFORMATION: Synthetic construct

<400> SEQUENCE: 35

Gly Leu Asn Asp Ile Phe Glu Ala Gln Lys Ile Glu Trp His Glu
1               5                   10                  15

<210> SEQ ID NO 36
<211> LENGTH: 21
<212> TYPE: DNA
<213> ORGANISM: Artificial sequence
<220> FEATURE:
<223> OTHER INFORMATION: Synthetic construct

<400> SEQUENCE: 36
gaaaatctgt attttcagag c          21

<210> SEQ ID NO 37
<211> LENGTH: 70
<212> TYPE: DNA
<213> ORGANISM: Artificial sequence
<220> FEATURE:
<223> OTHER INFORMATION: Synthetic construct

<400> SEQUENCE: 37
aatctcgagg gatctggatc cggaggtggc ggtagcgaaa atctgtattt tcagagctat          60
agcatggaac          70

<210> SEQ ID NO 38
<211> LENGTH: 29
<212> TYPE: DNA
<213> ORGANISM: Artificial sequence
<220> FEATURE:
<223> OTHER INFORMATION: Synthetic construct

<400> SEQUENCE: 38
aatgcggccg caaattccag cggaaatgc          29

<210> SEQ ID NO 39
<211> LENGTH: 34
<212> TYPE: DNA
<213> ORGANISM: Artificial sequence
<220> FEATURE:
<223> OTHER INFORMATION: Synthetic construct

<400> SEQUENCE: 39
ccaccatggc cggtctgaat gatatttttg aagc          34

<210> SEQ ID NO 40
<211> LENGTH: 25
<212> TYPE: DNA
<213> ORGANISM: Artificial sequence
<220> FEATURE:
<223> OTHER INFORMATION: Synthetic construct

```
<400> SEQUENCE: 40
ttgttctgcg gccgcaaatt ccagc                                              25

<210> SEQ ID NO 41
<211> LENGTH: 34
<212> TYPE: DNA
<213> ORGANISM: Artificial sequence
<220> FEATURE:
<223> OTHER INFORMATION: Synthetic construct

<400> SEQUENCE: 41
ccaccatggc cggtctgaat gatatttttg aagc                                    34

<210> SEQ ID NO 42
<211> LENGTH: 41
<212> TYPE: DNA
<213> ORGANISM: Artificial sequence
<220> FEATURE:
<223> OTHER INFORMATION: Synthetic construct

<400> SEQUENCE: 42
agagcggccg cttattaaaa ttccagcgga aatgcttctg c                            41

<210> SEQ ID NO 43
<211> LENGTH: 7
<212> TYPE: PRT
<213> ORGANISM: Artificial sequence
<220> FEATURE:
<223> OTHER INFORMATION: TEV protease restriction site
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 43

Glu Xaa Xaa Tyr Xaa Gln His
1               5
```